United States Patent [19]

Umezawa et al.

[11] 4,453,003
[45] Jun. 5, 1984

[54] PROCESS FOR PRODUCING THREO-3-AMINO-2-HYDROXY-BUTAN-OYL-AMINOACETIC ACIDS AS WELL AS NOVEL INTERMEDIATES THEREFOR AND PROCESS FOR PRODUCING THEM

[76] Inventors: Hamao Umezawa, No. 4-23, Toyotama-Kita, Nerima-ku, Tokyo; Takaaki Aoyagi, No. 3-3-6, Honkugenuma, Fujisawa-shi, Kanagawa-ken; Tadashi Shirai, No. 1-24-4, Naka-cho, Musashino-shi, Tokyo; Rinzo Nishizawa, No. 3-18-16, Sugano, Toshima-ku, Tokyo; Masao Suzuki, No. 2-28-36, Honan, Suginami-ku, Tokyo; Tetsushi Saino, No. 1039, Kamiochiai, Yono-shi, Saitama-ken, all of Japan

[21] Appl. No.: 336,492

[22] Filed: Dec. 31, 1981

Related U.S. Application Data

[62] Division of Ser. No. 211,035, Nov. 28, 1980, Pat. No. 4,391,986, which is a division of Ser. No. 96,693, Nov. 23, 1979, Pat. No. 4,281,180.

[30] Foreign Application Priority Data

Nov. 25, 1978 [JP] Japan ................................. 53-145509
Dec. 13, 1978 [JP] Japan ................................. 53-153157

[51] Int. Cl.³ .......................................... C07C 101/30
[52] U.S. Cl. ................................................. 562/448
[58] Field of Search ............................... 562/448, 439

[56] References Cited

U.S. PATENT DOCUMENTS 4,243,678  1/1981  Krastinat ............................ 562/448

FOREIGN PATENT DOCUMENTS 1510477  5/1978  United Kingdom .
1540019  2/1979  United Kingdom .

Primary Examiner—James H. Reamer

[57] ABSTRACT

A process for producing threo-3-amino-2-hydroxybutanoylaminoacetic acids comprises the steps of allowing to react a starting compound represented by the general formula:

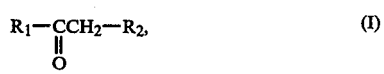

$$R_1-CCH_2-R_2, \quad (I)$$
$$\phantom{R_1-}\overset{\|}{O}$$

wherein $R_1$ represents a naphthyl or a group of the formula:

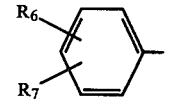

in which $R_6$ and $R_7$ represent individually hydrogen, halogen, amino or a protected amino, hydroxy or a protected hydroxy, a lower alkoxy or a lower alkyl and $R_2$ represents a protected amino, with a starting compound represented by the general formula:

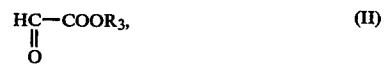

$$HC-COOR_3, \quad (II)$$
$$\overset{\|}{O}$$

wherein $R_3$ represents hydrogen or an ester residue, to obtain threo-3-protected amino-2-hydroxy-4-oxobutanoic acid or its ester represented by the general formula:

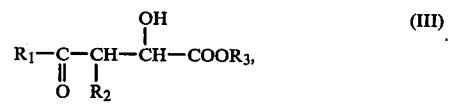

$$R_1-\underset{\underset{O}{\|}}{C}-\underset{\underset{R_2}{|}}{CH}-\overset{OH}{\overset{|}{CH}}-COOR_3, \quad (III)$$

wherein $R_1$, $R_2$ and $R_3$ have the same meanings as above, and then reducing the same into threo-3-protected amino-2-hydroxybutanoic acid or its ester represented by the general formula:

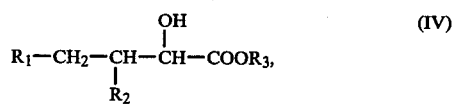

$$R_1-CH_2-\underset{\underset{R_2}{|}}{CH}-\overset{OH}{\overset{|}{CH}}-COOR_3, \quad (IV)$$

wherein $R_1$, $R_2$ and $R_3$ have the same meanings as above, and further converting the above compound into 3-amino-2-hydroxybutanoic acid represented by the general formula:

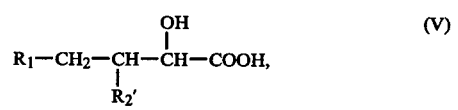

$$R_1-CH_2-\underset{\underset{R_2'}{|}}{CH}-\overset{OH}{\overset{|}{CH}}-COOH, \quad (V)$$

wherein $R_2'$ represents amino or a protected amino, thereafter condensing the same, in a conventional manner for forming a peptide coupling, with a compound represented by the general formula:

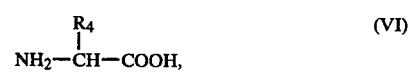

$$NH_2-\underset{\underset{}{|}}{\overset{R_4}{CH}}-COOH, \quad (VI)$$

wherein $R_4$ represents an alkyl having 3–4 carbon atom or 3-guanidinopropyl, while previously protecting as required those groups not relevant to the reaction, and removing the protecting groups for the functional groups to produce threo-3-amino-2-hydroxybutanoylaminoacetic acids represented by the general formula:
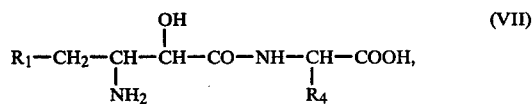
(VII)
wherein $R_1$ and $R_4$ have the same meanings as above.
This invention also provides the compounds represented by the general formula (III) as novel intermediates for the above aimed compounds and a process for producing the intermediates.
1 Claim, No Drawings

PROCESS FOR PRODUCING THREO-3-AMINO-2-HYDROXY-BUTANOYL-AMINOACETIC ACIDS AS WELL AS NOVEL INTERMEDIATES THEREFOR AND PROCESS FOR PRODUCING THEM

BACKGROUND OF THE INVENTION

This application is a divisional of application Ser. No. 211,035 filed Nov. 28, 1980, now U.S. Pat. No. 4,391,986, which is a divisional of Ser. No. 96,693, filed Nov. 23, 1979, now U.S. Pat. No. 4,281,180, issued July 28, 1981.

Most of threo-3-amino-2-hydroxybutanoylaminoacetic acids prepared according to this invention are known from U.S. Pat. Nos. 4,029,547 and 4,052,449, British Patent Nos. 1,510,477 and 1,540,019.

For example, (2S,3R)-3-amino-2-hydroxy-4-phenylbutanoylaminoacetic acid (herein after referred to simply as bestatin) is a least toxic substance isolated from culture filtrates of Streptomyces olivoreticuli as an aminopeptidase B inhibitor (referred to U.S. Pat. No. 4,029,547) by H. Umezawa, et al., which has been found to exhibit an increasing effect to immunoresponse such as delayed hypersthesia, activate in vivo defense mechanism and has inhibitive effects for cancer (referred to Japanese Patent Laid-Open Publication No. 117435/1977) and the compound is expected to be useful as a pharmaceutical.

It is also known that several 3-amino-2-hydroxybutanoylaminoacetic acids other than bestatin have equal or more inhibitory activity to aminopeptidase B than bestatin and a synthetic process therefor is disclosed in British Pat. No. 1,510,477. In the process described in the British patent, however, while (2S,3R)-3-amino-2-hydroxybutanoic acid, for example, as an intermediate for bestatin is synthesized through the steps shown below, the process has various defects as detailed later.

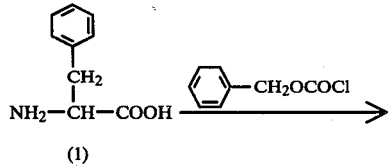

(1)

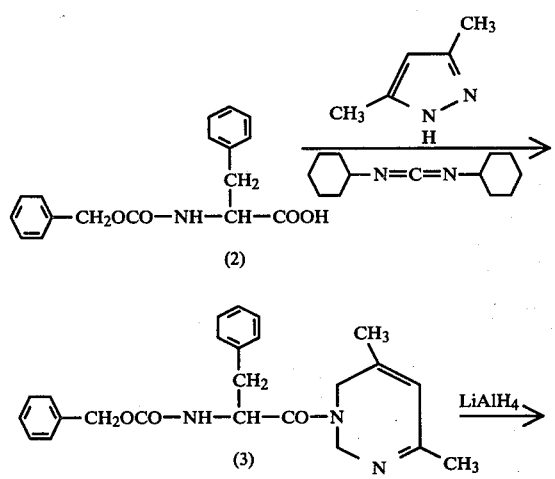

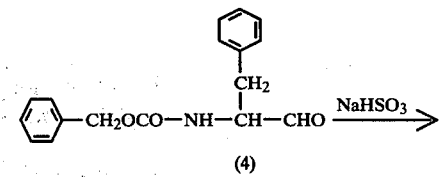

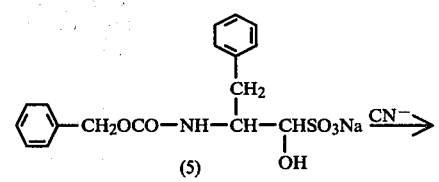

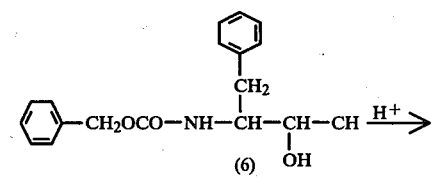

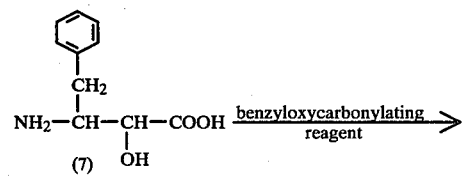

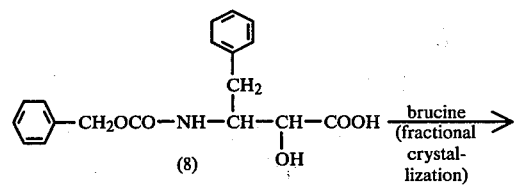

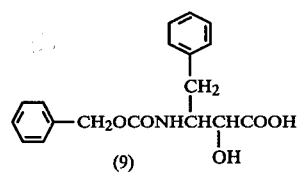

(R)-phenylalanine (1) is converted to a benzyloxycarbonyl derivative (2), which is then condensed with 3,5-dimethylpyrazole by using dicyclohexylcarbodiimide. The 3,5-dimethylpyrazolide (3) is reduced to benzyloxycarbonyl-(R)-phenylalaninal (4) with lithium aluminum hydride, which is then changed to the corresponding adduct (5) by reaction with sodium hydrogen sulfite and further to the cyanohydrin (6) through reaction with a cyanide. The above derivative is hydrolyzed under an acidic condition into (2RS,3R)-3-amino-2-hydroxy-4-phenylbutanoic acid (7), which is again allowed to react with a benzyloxycarbonylating reagent to convert to (2RS,3R)-3-benzyloxycarbonylamino-2-hydroxy-4-butanoic acid (8). The acid is fractionally crystallized into (2S,3R)-3-benzyloxycarbonylamino-2-hydroxy-4-phenylbutanoic acid (9) by using brucine.

Although the above process can be conducted with no troubles in a laboratory scale, it is not suited to large scale production so that the process includes the use of much expensive (R)-phenylalanine which is not a natural amino acid, the use of highly ignitable lithium aluminum hydride for the reduction of the pyrazolide, as well as the use of a very poisonous cyanide in synthesis of cyanohydrin.

In view of the above, the inventors have made an earnest study seeking for a process suited to mass production with no foregoing defects and, accomplished this invention.

The process according to this invention can produce the end products at a high yield without using an expensive amino acid such as (R)-phenylalanine and with no use of a cyanide, and thus it is much suited to the mass production.

SUMMARY OF THE INVENTION

This invention concerns a process for producing threo-3-amino-2-hydroxybutanoylaminoacetic acids and esters thereof which comprises the steps of:

(A) reacting a N-protected 2-oxoethylamine represented by the general formula:

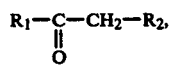

wherein $R_1$ represents a naphthyl or a group of the formula:

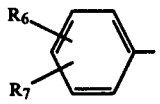

in which $R_6$ and $R_7$ individually represent hydrogen, halogen, amino or a protected amino, hydroxy or a protected hydroxy, a lower alkoxy, a lower alkyl or phenyl and $R_2$ represents a protected amino, with glyoxylic acid or its ester represented by the general formula:

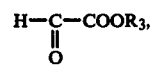

wherein $R_3$ represents hydrogen or an ester residue, to change into threo-3-protected amino-2-hydroxy-4-oxobutanoic acid or its ester represented by the general formula:

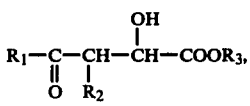

wherein $R_1$, $R_2$ and $R_3$ have the same meaning as above;

(B) reducing the above compound into threo-3-protected amino-2-hydroxybutanoic acid or its ester represented by the general formula:

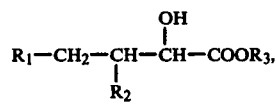

wherein $R_1$, $R_2$ and $R_3$ have the same meanings as above;

(C) subjecting the above compound, as may be required, to step(s) of (a) ester residue elimination, (b) optical resolution and/or (c) amino protecting group removal to obtain threo-3-amino-2-hydroxybutanoic acid represented by the general formula:

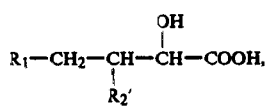

wherein $R_1$ has the same meaning as above and $R_2'$ represents amino or a protected amino, and (D) condensing the above compound in a conventional manner for the formation of a peptide coupling with an aminoacetic acid represented by the general formula:

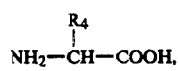

wherein $R_4$ represents an alkyl having 3–4 carbon atom number or 3-guanidinopropyl, after protecting, as required, functional group therein not relevant to the reaction and then removing the protecting group for the functional group to thereby prepare 3-amino-2-hydroxy-butanoylaminoacetic acid represented by the general formula:

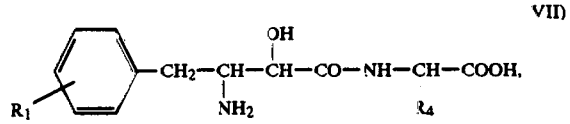

wherein $R_1$ and $R_4$ have the same meanings as above.

This invention also concerns threo-3-amino-2-hydroxy-4-oxobutanoic acids of the general formula (III) and esters thereof, a process for the production thereof, as well as a process for producing threo-3-protected amino-2-hydroxybutanoic acids of the general formula (IV).

DETAILED DESCRIPTION OF THE INVENTION

In the starting material of the general formula (I) in this invention, $R_1$ may be a naphthyl, for example, 1-naphthyl and 2-naphthyl or may be a group of the formula

in which $R_6$ and $R_7$ may be identical or different to each other.

$R_6$ and $R_7$ may be halogen such as chlorine, bromine and fluorine, a lower alkoxy having 1–6 carbon atom, for example, methoxy, ethoxy, ethoxy, propoxy, butoxy, pentyloxy and hexyloxy and a lower alkyl having 1–6 carbon atom, for example methyl, ethyl, propyl, butyl, penthyl and hexyl. The lower alkoxy or lower alkyl may be branched.

The group represented by the formula

includes, for example, phenyl, chlorophenyl, dichlorophenyl, fluorophenyl, aminophenyl, hydroxyphenyl, methoxyphenyl, ethoxyphenyl, n-propoxyphenyl, isopropoxyphenyl, n-butoxyphenyl, iso-butoxyphenyl, sec-butoxyphenyl, methylphenyl, n-propylphenyl, isopropylphenyl, n-butylphenyl, iso-butylphenyl, sec-butylphenyl, bipheyl, dihydroxyphenyl, dimethoxyphenyl and hydroxymethoxyphenyl. Substituents on the benzene nuclei may take any possible positions, that is, o-, m- or p-position; o- and m-positions, p- and o-positions or p- and m-positions.

The protecting group on the protected amino in $R_2$ includes an acyl, for example, formyl, a lower alkylcarbonyl which may have substituents such as halogen with no interference to the reaction, for example, acetyl, chloroacetyl, dichloroacetyl, bromoacetyl, 2-chloropropionyl and 2-bromopropionyl or benzoyl which may have substituents such as a lower alkoxy, a lower alkyl or halogen on the phenyl ring not interferring with the reaction; a lower alkyloxycarbonyl which may have substituents such as halogen not interferring with the reaction, for example, methoxycarbonyl, ethoxycarbonyl, iso-propyloxycarbonyl, iso-butyloxycarbonyl, t-butyloxycarbonyl, t-amyloxycarbonyl and 2,2,2-trichloroethoxycarbonyl, a cycloalkyloxycarbonyl, for example, cyclopentyloxycarbonyl and cyclohexyloxycarbonyl; a benzyloxycarbonyl which may have substituents such as a lower alkoxy, a lower alkyl and halogen on the phenyl ring not interferring with the reaction, for example, benzyl oxycarbonyl, chlorobenzyloxycarbonyl, nitrobenzyloxycarbonyl, methoxybenzyloxycarbonyl, methylbenzyloxycarbonyl; carbamoyl, a lower alkylcarbamoyl, for example, methylcarbamoyl, ethylcarbamoyl, propylcarbamoyl and butylcarbamoyl and phenylcarbamoyl, as well as phthalyl. The alkyl and phenyl in the phthalyl or carbamoyl may have substituents not interferring with the reaction.

The above protecting groups can also be used as the protecting groups for $R_6$ and $R_7$ if they are amino or hydroxy groups.

A N-protected 2-oxoethylamine of the general formula (I) employed as a starting material in this invention includes many novel compounds, and they can be synthesized, in the same manner as that for known compounds from a methylketon represented by the general formula:

$$R_1\text{—COCH}_3 \qquad (VIII),$$

wherein $R_1$ has the same meaning as above, by brominating it into a corresponding bromomethylketone, reacting the brominated ketone with hexamethylenetetramine, hydrolyzing it into a corresponding 2-oxoethylamine and then protecting the amino groups therein through reaction with an appropriate acylating agent.

The compound of the general formula (I) includes, sepcifically,
N-(2-oxo-2-phenylethyl)acetamide,
N-(2-oxo-2-phenylethyl)benzamide,
N-(2-oxo-2-phenylethyl)phthalimide,
2-methoxycarbonylaminoacetophenone,
2-t-butyloxycarbonylaminoacetophenone,
N-[2-oxo-2-(4-hydroxyphenyl)ethyl]acetamide,
N-[2-oxo-2-(4-hydroxyphenyl)ethyl]chloroacetamide,
2-ethoxycarbonylamino-4'-hydroxyacetophenone,
N-[2-oxo-2-(3-hydroxyphenyl)ethyl]benzamide,
2-t-butyloxycarbonylamino-3'-hydroxyacetophenone,
N-(2-oxo-2-phenylethyl)chloroacetamide,
2-t-butyloxycarbonylaminoacetophenone,
N-[2-oxo-2-(4-chlorophenyl)ethyl]acetamide,
N-[2-oxo-2-(3-chlorophenyl)ethyl]acetamide,
N-[2-oxo-2-(4-methylphenyl)ethyl]acetamide,
N-[2-oxo-2-(3-methylphenyl)ethyl]acetamide,
N-[2-oxo-2-(1-naphthyl)ethyl]acetamide,
N-[2-oxo-2-(2-naphthyl)ethyl]acetamide,
N-[2-oxo-2-(4-fluorophenyl)ethyl]acetamide,
N-[2-oxo-2-(4-bromophenyl)ethyl]acetamide,
N-[2-oxo-2-(2-methoxyphenyl)ethyl]acetamide,
N-[2-oxo-2-(3-methoxyphenyl)ethyl]acetamide,
N-[2-oxo-2-(4-methoxyphenyl)ethyl]acetamide,
N-[2-oxo-2-(2-ethoxyphenyl)ethyl]acetamide,
N-[2-oxo-2-(3-ethoxyphenyl)ethyl]acetamide,
N-[2-oxo-2-(4-ethoxyphenyl)ethyl]acetamide,
N-[2-oxo-2-(4-n-propoxyphenyl)ethyl]acetamide,
N-[2-oxo-2-(4-iso-propoxyphenyl)ethyl]acetamide,
N-[2-oxo-2-(4-n-butoxyphenyl)ethyl]acetamide,
N-[2-oxo-2-(4-isobutoxyphenyl)ethyl]acetamide,
N-[2-oxo-2-(4-sec-butoxyphenyl)ethyl]acetamide,
N-[2-oxo-2-(2-ethylphenyl)ethyl]acetamide,
N-[2-oxo-2-(3-ethylphenyl)ethyl]acetamide,
N-[2-oxo-2-(4-ethylphenyl)ethyl]acetamide,
N-[2-oxo-2-(4-n-propylphenyl)ethyl]acetamide,
N-[2-oxo-2-(4-iso-propylphenyl)ethyl]benzamide,
N-[2-oxo-2-(4-n-butylphenyl)ethyl]acetamide,
N-[2-oxo-2-(4-iso-butylphenyl)ethyl]benzamide,
N-[2-oxo-2-(4-sec-butylphenyl)ethyl]acetamide,
N-[2-oxo-2-(2-hydroxyphenyl)ethyl]acetamide,
N-[2-oxo-2-(3-hydroxyphenyl)ethyl]acetamide, and
N-[2-oxo-2-(3,4-dihydroxyphenyl)ethyl]acetamide.

The ester residues of $R_3$ in the compound represented by the general formula (II) have no particular restrictions so long as they result in no interference with the reaction and those employed usually include a lower alkyl having 1–6 carbon atom number such as methyl, ethyl, propyl, butyl, pentyl and hexyl or benzyl, in which these lower alkyl or benzyl group may have substituents such as halogen not interferring with the reaction.

The compound of the general formula (II) may include, for example, glyoxylic acid, its methyl, ethyl and benzyl esters.

The reaction of N-protected 2-oxoethylamine of the general formula (I) and glyoxylic acid or its ester of the general formula (II) in this invention is usually carried out in water, an organic solvent or a mixed solvent of water and an organic solvent in the presence of a base.

Organic solvents employed as the mixed solvent with water have no particular restriction so long as they are water-miscible and they, preferably, include polar solvents such as lower alcohols, for example, methanol, ethanol and propanol; ketones, for example, acetone and methylethylketone; acetonitrile, tetrahydrofuran, dioxane, dimethylformamide, dimethylacetamide, dimethylsulfoxide.

Organic solvents in which the reaction is conducted also have no particular restriction so long as they can dissolve the starting materials and they, preferably, include in addition to the solvents referred to above, esters, for example, a lower alkylester of acetic acid such as methyl acetate and ethyl acetate; ethers, for example, diethylether and diisopropylether, and halogenated hydrocarbons, for example, chloroform and carbontetrachloride.

The bases used herein include inorganic bases such as hydroxides, carbonates and hydrogen carbonates of alkali or alkaline earth metals, for example, potassium hydroxide, sodium hydroxide, calcium hydroxide, potassium carbonate, sodium carbonate, potassium hydrogen carbonate and sodium hydrogen carbonate, and ammonia; organic bases such as alkali metal salts of organic acids, for example, alkali metal salts of lower alkyl carboxylic acids such as potassium acetate, sodium acetate, sodium formate and potassium propionate, aromatic amines, for example, pyridine and aliphatic amine, for example, trimethylamine and triethylamine. For the reaction in water or a water-containing organic solvent, inorganic bases, particularly, hydrogen carbonates of alkali metals, for example, sodium hydrogen carbonate and potassium hydrogen carbonate are preferred. For the reaction in an organic solvent, are used organic bases, preferably, alkylamines and, in particular, triethylamine.

The amount of the bases employed has no particular restriction so long as the reaction solution is kept between slightly acidic and alkaline, and it is preferred to use them in an amount, for example, 0.5–10 mol, and usually, 1–2 mol per mol of glyoxylic acid or its ester represented by the general formula (II).

The reaction can be carried out at a reaction temperature from 0° C. to the boiling point of a solvent and, usually, from room temperature up to 60° C.

While the reaction time varies depending on the reaction temperature, starting compounds and the solvent, it is not determined specifically but the reaction is completed in about 2–100 hours and, usually, in about 12–20 hours at the reaction temperature from room temperature up to 60° C.

The glyoxylic acid or its ester represented by the general formula (II) used in this invention has not particular restriction in its amount and it is employed, usually, in a wide range between 0.2–10 mol and preferably, 1–2 mol per mol of N-protected 2-oxoethylamine represented by the general formula (I).

For the glyoxylic acid of the general formula (II) in which $R_3$ represents hydrogen atom, an inexpensive aqueous solution can be used with no troubles for the reaction.

Through the reaction of the compound of the general formula (I) and the compound of the general formula (II) in this way, the compound of the general formula (III) can be formed. The compound formed is isolated from the reaction mixture, for example, as follows.

(a) For the compound in which $R_3$ is hydrogen atom (1) If water is used for the reaction solvent, the reaction mixture is acidified with an acid to precipitate crystals, which are separated by filtration.

(2) If a mixed solvent of water and an organic solvent is used for the reaction solvent, the organic solvent is at first removed under reduced pressure and then the residue is made acidic by the addition of an acid to precipitate crystals, which are separated by filtration.

(b) For the compound in which $R_3$ is an ester residue

Since an organic solvent or a water-containing solvent is usually employed as the reaction solvent in this case, the reaction mixture is concentrated under reduced pressure after the reaction to remove the organic solvent. Then, water is added to the residue, which is then extracted with an organic solvent such as ethyl acetate. The ethyl acetate phase is washed with water and dried over a drying agent such as anhydrous sodium sulfate. The solvent is distilled off under reduced pressure, the residue is triturated with n-hexane and then precipitated crystals are collected by filtration.

All of the threo-(2RS)-3-amino-2-hydroxy-4-oxobutanoic acids or the esters thereof represented by the general formula (III) obtained are novel compounds and they include as typical examples:

threo-(2RS)-3-acetylamine-2-hydroxy-4-oxo-4-phenylbutanoic acid, ethyl ester of threo-(2RS)-3-acetylamine-2-hydroxy-4-oxo-4-phenylbutanoic acid, threo-(2RS)-3-chloroacetylamino-2-hydroxy-4-oxo-4-phenylbutanoic acid, methyl ester of threo-(2RS)-3-chloroacetylamino-2-hydroxy-4-oxo-4-phenylbutanoic acid, threo-(2RS)-3-methoxycarbonylamino-2-hydroxy-4-oxo-4-phenylbutanoic acid, threo-(2RS)-3-t-butoxycarbonylamino-2-hydroxy-4-oxo-4-phenylbutanoic acid, threo-(2RS)-3-benzoylamino-2-hydroxy-4-oxo-4-phenylbutanoic acid, threo-(2RS)-3-acetylamino-2-hydroxy-4-oxo-4-(4-hydroxyphenyl)butanoic acid, threo-(2RS)-3-benzoylamino-2-hydroxy-4-oxo-4-(4-hydroxyphenyl)butanoic acid, threo-(2RS)-3-acetylamino-2-hydroxy-4-oxo-4-(3-hydroxyphenyl)butanoic acid, threo-(2RS)-3-benzoylamino-2-hydroxy-4-oxo-4-(3-hydroxyphenyl)butanoic acid, threo-(2RS)-3-ethoxycarbonylamino-2-hydroxy-4-oxo-4-(4-hydroxyphenyl)butanoic acid, threo-(2RS)-3-t-butoxycarbonylamino-2-hydroxy-4-oxo-4-(3-hydroxyphenyl)butanoic acid, threo-(2RS)-3-acetylamino-2-hydroxy-4-oxo-4-(1-naphthyl)butanoic acid, threo-(2RS)-3-acetylamino-2-hydroxy-4-oxo-4-(2-naphthyl)butanoic acid, threo-(2RS)-3-acetylamino-2-hydroxy-4-oxo-4-(4-fluorophenyl)butanoic acid, threo-(2RS)-3-acetylamino-2-hydroxy-4-oxo-4-(4-bromophenyl)butanoic acid, threo-(2RS)-3-acetylamino-2-hydroxy-4-oxo-4-(2-methoxyphenyl)butanoic acid, threo-(2RS)-3-acetylamino-2-hydroxy-4-oxo-4-(3-methoxyphenyl)butanoic acid, threo-(2RS)-3-acetylamino-2-hydroxy-4-oxo-4-(4-methoxyphenyl)butanoic acid, methyl ester of threo-(2RS)-3-acetylamino-2-hydroxy-4-oxo-4-(4-methoxyphenyl)butanoic acid, threo-(2RS)-3-acetylamino-2-hydroxy-4-oxo-4-(2-ethoxyphenyl)butanoic acid, threo-(2RS)-3-acetylamino-2-hydroxy-4-oxo-4-(3-ethoxyphenyl)butanoic acid, threo-(2RS)-3-acetylamino-2-hydroxy-4-oxo-4-(4-ethoxyphenyl)butanoic acid, threo-(2RS)-3-acetylamino-2-hydroxy-4-oxo-4-(4-n-propoxyphenyl)butanoic acid, threo-(2RS)-3-acetylamino-2-hydroxy-4-oxo-(4-isopropoxyphenyl)butanoic acid, threo-(2RS)-3-acetylamino-2-hydroxy-4-oxo-4-(4-n-butoxyphenyl)butanoic acid, threo-(2RS)-3-acetylamino-2-hydroxy-4-oxo-4-(4-isobutoxyphenyl)butanoic acid, threo-(2RS)-3-acetylamino-2-hydroxy-4-oxo-4-(4-sec-butoxyphenyl)butanoic acid, threo-(2RS)-3-acetylamino-2-hydroxy-4-oxo-4-(2-ethylphenyl)butanoic acid,
threo-(2RS)-3-acetylamino-2-hydroxy-4-oxo-4-(3-ethylphenyl)butanoic acid,
threo-(2RS)-3-acetylamino-2-hydroxy-4-oxo-4-(4-ethylphenyl)butanoic acid,
threo-(2RS)-3-acetylamino-2-hydroxy-4-oxo-4-(4-n-propylphenyl)butanoic acid,
threo-(2RS)-3-benzoylamino-2-hydroxy-4-oxo-4-(4-isopropylphenyl)butanoic acid,
threo-(2RS)-3-acetylamino-2-hydroxy-4-oxo-4-(4-n-butylphenyl)butanoic acid,
threo-(2RS)-3-benzoylamino-2-hydroxy-4-oxo-4-(4-isobutylphenyl)butanoic acid,
threo-(2RS)-3-acetylamino-2-hydroxy-4-oxo-4-(4-sec-butylphenyl)butanoic acid,
threo-(2RS)-3-acetylamino-2-hydroxy-4-oxo-4-(2-hydroxyphenyl)butanoic acid,
threo-(2RS)-3-acetylamino-2-hydroxy-4-oxo-4-(3-hydroxyphenyl)butanoic acid, and
threo-(2RS)-3-acetylamino-2-hydroxy-4-oxo-4-(3,4-dihydroxyphenyl)butanoic acid.

The threo-(2RS)-3-protected amino-2-hydroxy-4-oxo-butanoic acid or its ester obtained and represented by the general formula (III) can be converted with ease to threo-(2RS)-3-amino-2-hydroxybutanoic acid or its ester represented by the general formula (IV) by reduction.

The reduction process used herein can be selected with no particular restriction provided that it can reduce the carbonyl group directly combined to an aromatic nuclei to methylene group and the process includes, for example, catalytic hydrogenation using palladium such as palladium black, palladium carbon and palladium barium sulfate or Raney nickel, reduction with lithium aluminum hydride, sodium bis(2-methoxyethoxy)aluminum hydride in the presence of anhydrous aluminum chloride, reduction with an acidic zinc or tin, and reduction with metal sodium or metal lithium in liquid ammonia. The catalytic hydrogenation using palladium such as palladium black and palladium carbon or Raney nickel is particularly preferred.

The reduction process using palladium or Raney nickel is carried out by dissolving or suspending threo-3-protected amino-2-hydroxy-4-oxobutanoic acid or its ester represented by the general formula (III) into a solvent and adding palladium or Raney nickel thereto, and reducing in a hydrogen atmosphere. The hydrogen may be used at an atmospheric pressure or an elevated pressure in an autoclave, and the reduction can be proceeded rapidly under an elevated pressure.

While the reaction solvent is not particularly restricted so long as it can dissolve threo-3-protected amino-2-hydroxy-4-oxobutanoic acid or its ester represented by the general formula (III) even in a small amount, the use of lower alcohols such as methanol ethanol and propanol, lower alkylcarboxylic acids such as acetic acid and propionic acid, water containing them or mixed solvents containing them with other organic solvents is preferred. While reaction temperature from 0° C. up to 150° C. can be used, the reaction is, preferably, carried out at 40°–100° C. in a solvent containing acetic acid or methanol 3-protected amino-2-hydroxybutanoic acid or its ester formed and represented by the general formula (IV) can be isolated with ease from the reaction mixture by filtrating out the catalyst, then concentrating the filtrate and adding an appropriate solvent to the residue to precipitate crystals and collecting the precipitated crystals by filtration.

Those compounds represented by the general formula (IV) in which $R_2$ is protected by the protecting groups such as chloroacetyl, dichloroacetyl, t-butoxycarbonyl, t-pentyloxycarbonyl, 2,2,2-trichloroethoxycarbonyl, cyclopentyloxycarbonyl, cyclohexyloxycarbonyl, and phthalyl are especially preferred since, after optical resolution as required, they can be allowed to directly react with aminoacetic acid of the general formula (VI) to prepare threo-3-amino-2-hydroxybutanolacetic acid represented by the general formula (VII).

Threo-3-protected amino-2-hydroxybutanoic acid or its ester represented by the general formula (IV) includes as its typical examples:
threo-(2RS)-3-acetylamino-2-hydroxy-4-phenylbutanoic acid,
ethyl ester of threo-(2RS)-3-acetylamino-2-hydroxy-4-phenyl-butanoic acid,
threo-(2RS)-3-benzoylamino-2-hydroxy-4-phenylbutanoic acid,
threo-(2RS)-3-chloroacetylamino-2-hydroxy-4-phenylbutanoic acid,
methyl ester of threo-(2RS)-3-chloroacetylamino-2-hydroxy-4-phenylbutanoic acid,
threo-(2RS)-3-methoxycarbonylamino-4-phenylbutanoic acid,
threo-(2RS)-3-t-butoxycarbonylamino-4-phenylbutanoic acid,
threo-(2RS)-3-phthalimino-4-phenylbutanoic acid,
threo-(2RS)-3-acetylamino-2-hydroxy-4-(4-hydroxyphenyl)butanoic acid,
threo-(2RS)-3-benzoylamino-2-hydroxy-4-(4-hydroxyphenyl)butanoic acid,
threo-(2RS)-3-acetylamino-2-hydroxy-4-(3-hydroxyphenyl)butanoic acid,
threo-(2RS)-3-benzoylamino-2-hydroxy-4-(3-hydroxyphenyl)butanoic acid,
threo-(2RS)-3-acetylamino-2-hydroxy-4-(2-hydroxyphenyl)butanoic acid,
threo-(2RS)-3-benzoylamino-2-hydroxy-4-(2-hydroxyphenyl)butanoic acid,
threo-(2RS)-3-acetylamino-2-hydroxy-4-(1-naphthyl)-butanoic acid,
threo-(2RS)-3-acetylamino-2-hydroxy-4-(2-naphthyl)-butanoic acid,
threo-(2RS)-3-acetylamino-2-hydroxy-4-(4-fluorophenyl)butanoic acid,
threo-(2RS)-3-acetylamino-2-hydroxy-4-(4-bromophenyl)butanoic acid,
threo-(2RS)-3-acetylamino-2-hydroxy-4-(2-methoxyphenyl)butanoic acid,
threo-(2RS)-3-acetylamino-2-hydroxy-4-(3-methoxyphenyl)butanoic acid,
threo-(2RS)-3-acetylamino-2-hydroxy-4-(4-methoxyphenyl)butanoic acid,
methyl ester of threo-(2RS)-3-acetylamino-2-hydroxy-4-(4-methoxyphenyl)butanoic acid,
threo-(2RS)-3-acetylamino-2-hydroxy-4-(2-ethoxyphenyl)butanoic acid,
threo-(2RS)-3-acetylamino-2-hydroxy-4-(3-ethoxyphenyl)butanoic acid,
threo-(2RS)-3-acetylamino-2-hydroxy-4-(4-ethoxyphenyl)butanoic acid,
threo-(2RS)-3-acetylamino-2-hydroxy-4-(4-n-propoxyphenyl)butanoic acid, threo-(2RS)-3-acetylamino-2-hydroxy-4-(4-iso-propoxyphenyl)butanoic acid,
threo-(2RS)-3-acetylamino-2-hydroxy-4-(4-n-butoxyphenyl)butanoic acid,
threo-(2RS)-3-acetylamino-2-hydroxy-4-(4-iso-butoxyphenyl)butanoic acid,
threo-(2RS)-3-acetylamino-2-hydroxy-4-(4-sec-butoxyphenyl)butanoic acid,
threo-(2RS)-3-acetylamino-2-hydroxy-4-(2-ethylphenyl)butanoic acid,
threo-(2RS)-3-acetylamino-2-hydroxy-4-(3-ethylphenyl)butanoic acid,
threo-(2RS)-3-acetylamino-2-hydroxy-4-(4-ethylphenyl)butanoic acid,
threo-(2RS)-3-acetylamino-2-hydroxy-4-(4-n-propylphenyl)butanoic acid,
threo-(2RS)-3-benzoylamino-2-hydroxy-4-(4-iso-propylphenyl)butanoic acid,
threo-(2RS)-3-acetylamino-2-hydroxy-4-(4-n-butylphenyl)butanoic acid,
threo-(2RS)-3-benzoylamino-2-hydroxy-4-(4-isobutylphenyl)butanoic acid,
threo-(2RS)-3-acetylamino-2-hydroxy-4-(4-sec-butylphenyl)butanoic acid,
threo-(2RS)-3-acetylamino-2-hydroxy-4-(2-hydroxyphenyl)butanoic acid,
threo-(2RS)-3-acetylamino-2-hydroxy-4-(3-hydroxyphenyl)butanoic acid,
threo-(2RS)-3-acetylamino-2-hydroxy-4-(3,4-dihydroxyphenyl)butanoic acid,
and (2S,3R) type optical isomers thereof, as well as lower alkyl esters, for example, methyl, ethyl, propyl and butyl esters; and benzyl and chlorobenzyl esters of these acids.

If the compounds represented by the general formula (IV) are esters, they can be converted to threo-3-amino-2-hydroxybutanoic acids of the general formula (IV) by removing the ester residues in a conventional manner such as hydrolysis or reduction and further eliminating, if required, the amino protecting groups.

A threo-(2RS) compound represented by the general formula (IV) may be optically resolved to (2S,3R) and (2R,3S) isomers as required. In the case of a compound of the general formula (IV), in which $R_3$ is hydrogen, (a) it is directly resolved with an optically active base such as brucine and S(−)-or R(+)-1-phenylethylamine, (b) it is resolved with an optically active sulfonic acid such as camphorsulfonic acids or bromocamphorsulfonic acids after an amino protecting group in the compound is removed in the usual manner. In the case of a compound of the general formula (IV), in which $R_3$ is an ester residue, (c) it is resolved in the above-mentioned procedure after the ester residue is remove in the usual manner or (d) it is resolved with an optically active acid such as tartaric acid derivatives and camphorsulfonic acids after an amino protecting group is removed by the general method.

The solvent used in the optical resolution is properly selected depending on the compound of the general formula (IV) and the type of a resolving reagent.

If a (2S,3R) isomer obtained has an ester residue, it can be converted to (2S,3R)-amino-2-hydroxybutanoic acid represented by the general formula (V) by elimination of the ester residue in a conventional manner.

Condensation of compound represented by the general formula (IV) or (V) and aminoacetic acid of the general formula (VI) is carried out in a conventional manner for the formation of peptide linkage while protecting those functional groups not relevant to the reaction as required.

3-amino-2-hydroxybutanoylaminoacetic acid represented by the general formula (VII) which is the aimed compound of this invention can be prepared by removing the protecting groups for the functional groups after the end of the condensing reaction.

Protection for the functional groups not relevant to the reaction, for example, the protections for the amino group of $R_2'$ in the compound of the general formula (V) and for the carboxyl group in the compound of the general formula (VI) can be conducted in a conventional manner. The protection for the amino group, for example, with benzyloxycarbonyl group can be conducted by reaction of the compound of the general formula (V) in which $R_2'$ is an amino group and benzyloxycarbonyl chloride in Schotten-Baumann procedure, or reaction with benzyloxycarbonylating agent such as p-nitrophenyl benzyloxycarbonate, benzyloxycarbonylazide, benzyloxycarbonyl N-hydroxysuccinimide ester, benzyl S-4,6-dimethylpyrimide-2-yl-thiocarbonate, in the presence of a tertially organic base such as triethylamine or N-methylmorpholine in an aqueous organic solvent, for example, dioxane, tetrahydrofuran, acetonitril or dimethylformamide.

The condensing methods between the acid of the general formula (V) and the aminoacetic acid of the general formula (VI) include, for example, a carbodiimide process using dicyclohexylcarbodiimide and 1-ethyl-3-(3-dimethylaminopropyl)-carbodiimide, an azide process, a mixed acid anhydride process using ethyl chloroformate and isobutyl chloroformate, an active ester process using cyanomethyl ester, vinyl ester, substituted and non-substituted phenyl ester, thiophenyl ester and hydroxysuccinimide ester, an O-acylhydroxylamine derivative process using acetoxime and cyclohexanone oxime, an N-acyl compound process using carbodiimidazole.

Solvents employed in formation of the usual peptide linkage may be also used as the solvents for the condensation in this invention. The following solvents can, for example, be used; ethers such as diethylether, tetrahydrofuran and dioxane, esters such as ethyl acetate and methyl acetate, ketones such as acetone and methylethylketone, halogenated hydrocarbons such as methylene chloride and chloroform, amides such as dimethylformamide and dimethylacetamide and nitriles such as acetonitrile.

After the end of the condensing reaction, protecting groups are removed in the usual manner for the elimination of the protecting groups in the peptide chemistry such as catalytic reduction using palladium as a catalyst, acidolysis with hydrogen bromide in acetic acid, trifluoroacetic acid, hydrogen fluoride, hydrogen chloride in an organic solvent, saponification with an alkali, reducting with metal sodium in liquid ammonia.

The representative examples of the finally aimed products represented by the general formula (VII) are as follows:
threo-(2RS)-3-amino-2-hydroxy-4-(1-naphthyl)butanoyl-(S)-leucine,
threo(2RS)-3-amino-2-hydroxy-4-(2-naphthyl)butanoyl-(S)-leucine,
threo-(2RS)-3-amino-2-hydroxy-4-(4-fluorophenyl)butanoyl-(S)-leucine,
threo-(2RS)-3-amino-2-hydroxy-4-(2-methoxyphenyl)butanoyl-(S)-leucine, threo-(2RS)-3-amino-2-hydroxy-4-(3-methoxyphenyl)-butanoyl-(S)-leucine,
threo-(2RS)-3-amino-2-hydroxy-4-(4-methoxyphenyl)-butanoyl-(S)-leucine,
threo-(2RS)-3-amino-2-hydroxy-4-(2-ethoxyphenyl)butanoyl-(S)-leucine,
threo-(2RS)-3-amino-2-hydroxy-4-(3-ethoxyphenyl)butanoyl-(S)-leucine,
threo-(2RS)-3-amino-2-hydroxy-4-(4-ethoxyphenyl)butanoyl-(S)-leucine,
threo-(2RS)-3-amino-2-hydroxy-4-(4-n-propoxyphenyl)butanoyl-(S)-leucine,
threo-(2RS)-3-amino-2-hydroxy-4-(4-iso-propoxyphenyl)butanoyl-(S)-leucine,
threo-(2RS)-3-amino-2-hydroxy-4-(4-n-butoxyphenyl)-butanoyl-(S)-leucine,
threo-(2RS)-3-amino-2-hydroxy-4-(4-iso-butoxyphenyl)butanoyl-(S)-leucine,
threo-(2RS)-3-amino-2-hydroxy-4-(4-sec-butoxyphenyl)-butanoyl-(S)-leucine,
threo-(2RS)-3-amino-2-hydroxy-4-(2-ethylphenyl)butanoyl-(S)-leucine,
threo-(2RS)-3-amino-2-hydroxy-4-(3-ethylphenyl)butanoyl-(S)-leucine,
threo-(2RS)-3-amino-2-hydroxy-4-(4-ethylphenyl)butanoyl-(S)-leucine,
threo-(2RS)-3-amino-2-hydroxy-4-(4-n-propylphenyl)-butanoyl-(S)-leucine,
threo-(2RS)-3-amino-2-hydroxy-4-(4-iso-propylphenyl)butanoyl-(S)-leucine,
threo-(2RS)-3-amino-2-hydroxy-4-(4-n-butylphenyl)butanoyl-(S)-leucine,
threo-(2RS)-3-amino-2-hydroxy-4-(4-iso-butylphenyl)-butanoyl-(S)-leucine,
threo-(2RS)-3-amino-2-hydroxy-4-(4-sec-butylphenyl)-butanoyl-(S)-leucine,
threo-(2RS)-3-amino-2-hydroxy-4-(2-hydroxyphenyl)-butanoyl-(S)-leucine,
threo-(2RS)-3-amino-2-hydroxy-4-(3-hydroxyphenyl)-butanoyl-(S)-leucine,
threo-(2RS)-3-amino-2-hydroxy-4-(3,4-dihydroxyphenyl)butanoyl-(S)-leucine,
threo-(2RS)-3-amino-2-hydroxy-4-(4-chlorophenyl)butanoyl-(S)-leucine, and
threo-(2RS)-3-amino-2-hydroxy-4-(3-chlorophenyl)butanoyl-(S)-leucine,
or those compounds in which threo-(2RS) configuration is replaced with (2S,3R) form and (S)-leucine is replaced with (RS)- or (R)-leucine, (S)-, (RS- or (R)-valine, (S)-, (RS)- or (R)-norvaline, (S)-, (RS)- or (R)-isoleucine, (S)-, (RS)- or (R)-norleucine, (S)-, (RS)- or (R)-tert-leucine or (S)-, (RS)- or (R)-arginine, especially
(2S,3R)-3-amino-2-hydroxy-4-(4-aminophenyl)butanoyl-(S)-leucine,
(2S,3R)-3-amino-2-hydroxy-4-phenylbutanoyl-(S)-leucine(bestatin),
(2S,3R)-3-amino-2-hydroxy-4-(2-hydroxyphenyl)butanoyl-(S)-leucine(o-hydroxybestatin),
(2S,3R)-3-amino-2-hydroxy-4-(3-hydroxyphenyl)butanoyl-(S)-leucine(m-hydroxybestatin),
(2S,3R)-3-amino-2-hydroxy-4-(4-hydroxyphenyl)butanoyl-(S)-leucine(p-hydroxybestatin),
(2S,3R)-3-amino-2-hydroxy-4-(4-methoxyphenyl)butanoyl-(S)-leucine,
(2S,3R)-3-amino-2-hydroxy-4-phenylbutanoyl-(S)-valine,
(2S,3R)-3-amino-2-hydroxy-4-phenylbutanoyl-(S)-norvaline,
(2S,3R)-3-amino-2-hydroxy-4-phenylbutanoyl-(S)-arginine, and
(2S,3R)-3-amino-2-hydroxy-4-(4-hydroxyphenyl)butanoyl-(S)-arginine,
as well as physiologically non-toxic salts thereof, for example, salts of hydrochloric acid and acetic acid.

The above-mentioned compounds include many novel compounds together with several known compounds. As these novel compounds have inhibitory effect against aminopeptidase B, inhibit the formation of bradykinin and exhibit anti-inflammatory effects as the known compounds, they are expected to be useful as pharmaceutical medicine for various deceases.

Among the compounds of the general formula (VII) which are prepared according to this invention, those compound are novel wherein $R_1$ represents a naphthyl or a group of the formula

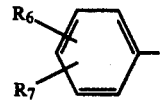

in which $R_7$ represents hydrogen and $R_6$ represents fluorine, lower alkyl (excepting methyl), lower alkyloxy, phenyl, m- or o-hydroxy, or both of $R_6$ and $R_7$ represent groups other than hydrogen, and the aminopeptidase B inhibitory activity of the representative compounds is as follows.

Inhibitory Activity to Aminopeptidase B

Test Method:

Measurement for the inhibitory activity to aminopeptidase B was conducted by the method reported by Hopsu et al. while somewhat modifying the process (V. K. Hopsu, K. K. Makinen, G. G. Glenner; Archives of Biochemistry and Biophysics, 114, 557 (1966)].

A mixed solution (pH 7.0) prepared by adding 1.0 ml of a 0.1 M tris-hydrochloric acid buffer solution and 0.7 ml of a solution containing a test specimen to 0.3 ml of 0.1 mM arginine-β-naphthylamide was heated at 37° C. for 4 minutes. Thereafter, 0.2 ml of an aminopeptidase B solution purified by the same enzyme purification process as in the process by Hopsu et al. using Sephadex G-100 (registered Trademark) was added and reacted at 37° C. for 30 minutes. Then, 0.6 ml of a 0.1 M acetic acid buffer solution (pH 4.2) containing Garnet GBC (o-aminoazotoluenediazonium salt) at 1.0 mg/ml concentration and containing Tween 20 (registered trademark) at 1.0% concentration was further added and left for 15 minutes at room temperature, after which absorption ratio (a) at 530 nm was measured. The absorption ratio (b) for the blind solution using only the buffer solution containing no specimen was simultaneously measured, and the inhibitory ratio to aminopeptidase B was calculated as $(b-a)/b \times 100$.

Result:

Inhibitory ratios for each of the specimens at several concentrations were determined by the above test method, from which 50% inhibitory ratios ($IC_{50}$) were deduced. The results are shown in Table 1.

TABLE 1

| No. | Compound | $IC_{50}(\mu g/ml)$ |
|---|---|---|
| 1. | (2S,3R)-3-amino-2-hydroxy-4-(4-methoxyphenyl)butanoyl-(S)-leucine | 0.006 |
| 2. | Threo-(2RS)-3-amino-2-hydroxy-4-(2-methoxyphenyl)butanoyl-(S)-leucine | 2.9 |

TABLE 1-continued

| No. | Compound | IC$_{50}$(μg/ml) |
|---|---|---|
| 3. | Threo-(2RS)-3-amino-2-hydroxy-4-(3-methoxyphenyl)butanoyl-(S)-leucine | 0.04 |
| 4. | Threo-(2RS)-3-amino-2-hydroxy-4-(1-naphthyl)butanoyl-(S)-leucine | 1.5 |
| 5. | Threo-(2RS)-3-amino-2-hydroxy-4-(2-naphthyl)butanoyl-(S)-leucine | 0.10 |
| 6. | Threo-(2RS)-3-amino-2-hydroxy-4-(4-phenyphenyl)butanoyl-(S)-leucine | 3.6 |
| 7. | Threo-(2RS)-3-amino-2-hydroxy-4-(4-isopropylphenyl)butanoyl-(S)-leucine | 0.12 |
| 8. | Threo-(2RS)-3-amino-2-hydroxy-4-(4-isobutylphenyl)butanoyl-(S)-leucine | 2.8 |
| 9. | Threo-(2RS)-3-amino-2-hydroxy-4-(3,4-dihydroxyphenyl)butanoyl-(S)-leucine | 1.8 |
| 10. | Threo-(2RS)-3-amino-2-hydroxy-4-(4-isopropoxyphenyl)butanoyl-(S)-leucine | 6.8 |
| 11. | Threo-(2RS)-3-amino-2-hydroxy-4-(4-isobutoxyphenyl)butanoyl-(S)-leucine | 4.5 |
| 12. | Threo-(2RS)-3-amino-2-hydroxy-4-(4-fluorophenyl)butanoyl-(S)-leucine | 0.03 |
| 13. | Threo-(2RS)-3-amino-2-hydroxy-4-(2-naphthyl)butanoyl-(S)-isoleucine | 0.03 |
| 14. | (2S,3R)-3-amino-2-hydroxy-4-(4-methoxyphenyl)butanoyl-(S)-valine | 0.07 |
| 15. | Threo-(2RS)-3-amino-2-hydroxy-4-(2-hydroxyphenyl)butanoyl-(S)-leucine | 0.53 |
| 16. | Threo-(2RS)-3-amino-2-hydroxy-4-(3-hydroxyphenyl)butanoyl-(S)-leucine | 0.09 |

This invention is to be described specifically by way of examples.

EXAMPLE 1

(1) Preparation of threo-(2RS)-3-acetylamino-2-hydroxy-4-oxo-4-(4-methoxyphenyl)butanoic acid N-[2-oxo-2-(4-methoxyphenyl)ethyl]acetamide (82.8 g, 0.400 mol), 95.8 g (1.14 mol) of sodium hydrogen carbonate and 66.3 g (0.720 mol) of glyoxylic acid monohydrate were dissolved in a mixture of 700 ml of methanol and 200 ml of water. When the solution was allowed to react at 50°–60° C., the reaction was complete after 4 hours. The reaction mixture was concentrated under reduced pressure to dryness. The residue was dissolved in water and then washed with ethyl acetate. The aqueous phase was adjusted with hydrochloric acid to pH 1–2. Deposited crystals were collected by filtration, washed with water and dried in vacuo. Threo-(2RS)-3-acetylamino-2-hydroxy-4-oxo-4-(4-methoxyphenyl)butanoic acid was obtained.

Yield 102.3 g (91.0%).

Mp. 193°–195° C. (decomposition).

NMR Spectrum (DMSO-d$_6$)δ=1.9 (s,3H; CH$_3$—CO), 3.8 (s,3H; CH$_3$—O), 4.5 (d,H,J=4 Hz; C$\underline{H}$—OH), 5.7 (dd, H; C$\underline{H}$—NH), 7.1, 7.9 (d, d, 2H, 2H, J = 9Hz; 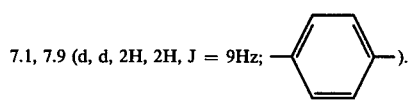 ).

(2) Preparation of threo-(2RS)-3-acetylamino-2-hydroxy-4-(4-methoxyphenyl)butanoic acid Threo-(2RS)-3-acetylamino-2-hydroxy-4-oxo-4-(4-methoxyphenyl)butanoic acid (30.0 g, 0.107 mol) was dissolved in 300 ml of methanol and 1.50 g of 5% palladium carbon was added. When the solution was reduced in an autoclave at a temperature of 40° C. and at a hydrogen pressure of 25 kg/cm$^2$, the reaction was completed after about 3 hours.

The catalyst was removed by filtration and the filtrate was concentrated under reduced pressure. To the residue was added 100 ml of ethyl acetate and precipitated crystals were collected by filtration, washed with ethyl acetate and dried in vacuo. Threo-(2RS)-3-acetylamino-2-hydroxy-4-(4-methoxyphenyl)butanoic acid was obtained.

Yield 26.5 g (92.7%).

Mp. 174°–176° C.

NMR Spectrum (CF$_3$ COOD), δ=2.3 (s, 3H; CH$_3$—CO), 3.1 (d, 2H, J=8 Hz; CH$_2$), 4.0 (s, 3H; CH$_3$—O), 4.6 (d, H, J=2 Hz; C$\underline{H}$—OH), 7.0, 7.3 (d, d, 2H, 2H, J = 9Hz; 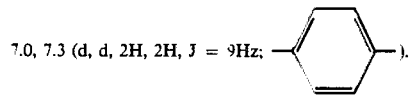 ).

(3) Preparation of (2S,3R)-3-acetylamino-2-hydroxy-4-(4-methoxyphenyl)butanoic acid Threo-(2RS)-3-acetylamino-2-hydroxy-4-(4-methoxyphenyl)butanoic acid (10.0 g, 37.0 mmol) and 4.8 g (37.0 mmol) of S(—)-1-phenylethylamine were dissolved under heating in 75 ml of ethanol. They were then allowed to cool at room temperature. Deposited crystals were collected by filtration, washed with a small amount of ethanol and dried in vacuo. 4.56 g of crystals were obtained.

[α]$_D^{20}$+32.1° (c=1.9, methanol).

The crystals (4.50 g) were dissolved in 30 ml of ethanol under heating and allowed to cool to room temperature. Precipitated crystals were collected by filtration, washed with a small amount of ethanol and dried. The S(—)-1-phenylethylamine salt of (2S,3R)-3-acetylamino-2-hydroxy-(4-methoxyphenyl)butanoic acid was obtained.

Yield 4.24 g. Mp. 194°–195° C.

[α]$_D^{20}$+32.8° (c=0.5, methanol).

(4) Preparation of (2S,3R)-3-acetylamino-2-hydroxy-4-(4-methoxyphenyl)butanoic acid The S(—)-phenylethylamine salt of (2S,3R)-2-acetylamino-2-hydroxy-4-(4-methoxyphenyl)butanoic acid (2.79 g, 7.20 mmol) was added to 15 ml of 0.5 N sodium hydroxide aqueous solution and S(—)-1-phenylethylamine was extracted by the addition of each 15 ml of ethyl acetate for three times.

The aqueous phase was separated and adjusted with N hydrochloric acid to pH 1–2 and concentrated to dryness under reduced pressure. To the residue was added 20 ml of acetone, insoluble compounds were removed hyfiltration and then the filtrate was concentrated to dryness under reduced pressure. Ethyl acetate (30 ml) was added to the residue. Deposited crystals were collected by filtration, washed with ethyl acetate and dried anoic invacuo. (2S,3R)-3-acetylamino-2-hydroxy-4-(4-methoxyphenyl)butanoic acid was obtained.

Yield 1.32 g (68.1%).

[α]$_D^{22}$+27.7° (c=1.1, methanol).

(5) Preparation of (2S,3R)-3-amino-2-hydroxy-4-(4-methoxyphenyl)-butanoic acid (2S,3R)-3-acetylamino-2-hydroxy-4-(4-methoxyphenyl)butanoic acid (4.89 g, 18.3 mmol) was added to a mixture of 22 ml of 2.5 N hydrochloric acid and 22 ml of dioxane. When the solution was heated at 60° C., the reaction was completed after 8 hours.

The reaction solution was concentrated under reduced pressure to dryness. The residue was dissolved in water and again concentrated under reduced pressure to dryness. The residue was dissolved in 20 ml of water and insoluble compounds were separated out by filtration. Then, the aqueous phase was adjusted with 2 N sodium hydroxide aqueous solution to pH 5-6 and chilled in an ice bath. Precipitated crystals were collected by filtration, washed with water and dried in vacuo. (2S,3R)-3-amino-2-hydroxy-4-(4-methoxyphenyl)butanoic acid was obtained.

Yield 3.28 g (79.6%).
$[\alpha]_D^{20} +26.9°$ (c=1, N HCl).
Mp. 230°–232° C. (decomposition).
NMR Spectrum ($CF_3COOD$) $\delta$=3.2 (dd, 2H; $CH_2$), 3.9 (s, 3H; $CH_3$), 4.2 (multi, H; C$\underline{H}$—$NH_2$), 4.8 (d, H, J=4 Hz; C$\underline{H}$—OH), 7.1, 7.3 (d, d, 2H, 2H, J = 9Hz; 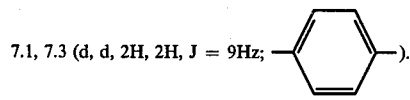).

(6) Preparation of (2S,3R)-3-benzyloxycarbonylamino-2-hydroxy-4-(4-methoxyphenyl)butanoic acid (2S,3R)-3-amino-2-hydroxy-4-(4-methoxyphenyl)-butanoic acid (2.70 g, 12.0 mmol), 2.52 ml (18.0 mmol) of triethylamine and 3.95 g (14.4 mmol) of benzyl S-4,6-dimethylpyrimidin-2-ylthiocarbonate were dissolved in a mixed solvent of 12 ml of water and 12 ml of dioxane.

The reaction was completed through stirring overnight at room temperature. The reaction solution was concentrated under reduced pressure in order to distil off dioxane. To the residue was added 50 ml of water and the solution was washed with each 50 ml of ethyl acetate twice. The aqueous phase was adjusted with diluted hydrochloric acid to pH 1–2. Deposited oily products were extracted twice each with 50 ml of ethyl acetate. The extracts were combined, washed with each 50 ml of a aqueous solution of sodium chloride for three times and then dried over anhydrous sodium sulfate.

The sodium sulfate was removed by filtration. The filtrate was concentrated under reduced pressure and the residue was triturated with petroleum ether. Separated crystals were collected by filtration, washed with petroleum ether and dried in vacuo. (2S,3R)-3-benzyloxycarbonylamino-2-hydroxy-4-(4-methoxyphenyl)-butanoic acid was obtained.

Yield 3.25 g (75.4%). Mp. 160°–162° C.
$[\alpha]_{578}^{27} +87.1°$ (c=1, acetic acid).
NMR Spectrum (DMSO-$d_6$) $\delta$=2.8 (d, 2H, J=6 Hz; $CH_2$—CH), 3.7 (s, 3H; $CH_3$) 4.0 (d, H, J=2 Hz; C$\underline{H}$—OH), 4.1 (multi, H; C$\underline{H}$—NH), 5.0 (s, 2H; $CH_2$—O), 7.1 (multi, 10H; 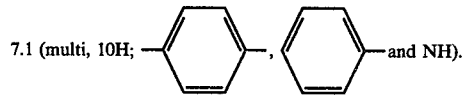 and NH).

(7) Preparation of (2S,3R)-3-benzyloxycarbonylamino-2-hydroxy-4-(4-methoxyphenyl)butanoyl-(S)-leucine benzyl ester (2S,3R)-3-benzyloxycarbonylamino-2-hydroxy-4-(4-methoxyphenyl)butanoic acid (1.44 g, 4.00 mmol), 1.91 g (4.80 mmol) of the p-toluenesulfonic acid salt of benzyl (S)-leucinate and 0.65 g (4.8 mmol) of 1-hydroxybenzotriazole were dissolved in 23 ml of tetrahydrofuran. While cooling in an ice-salt bath, 0.67 ml (4.8 mmol) of triethylamine and 0.99 g (4.8 mmol) of dicyclohexylcarbodiimide were added to the solution and allowed to react overnight.

Separated dicyclohexylurea was filtered off and the filtrate was concentrated under reduced pressure. The residue was dissolved in 40 ml of ethyl acetate and insoluble products were separated by filtration once more and washed with ethyl acetate. The filtrate and washing solution were joined and washed with 0.5 N hydrochloric acid twice, an aqueous solution of sodium chloride for three times, 5% aqueous solution of sodium hydrogen carbonate twice and an aqueous solution of common salt for three times successively and then dried over anhydrous sodium sulfate.

The sodium sulfate was separated out by filtration and the filtrate was concentrated under reduced pressure. The residue was triturated with n-hexane and precipitated crystals were collected by filtration, washed with n-hexane and dried in vacuo. The benzyl ester of (2S,3R)-3-benzyloxycarbonylamino-2-hydroxy-4-(4-methoxyphenyl)butanoyl-(S)-leucine was obtained.

Yield 2.21 g (98.2%). Mp. 124°–126° C.
$[\alpha]_{578}^{27} +21.6°$ (c=1, acetic acid).
NMR Spectrum ($CDCl_3$) $\delta$=0.9 (d, 6H, J=5 Hz; $(CH_3)_2CH$) 2.9 (d, 2H, J=8 Hz; CH—$CH_2$—Ar), 3.7 (s, 3H; $CH_3$—O), 5.0, 5.1 (s, s, 2H, 2H; $CH_2$—OCOCH, $CH_2$—OCONH) 5.5 (d, H, J=9 Hz; N$\underline{H}$), 7.0 (multi, 15H; 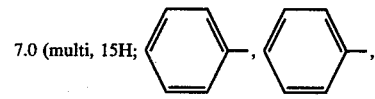, 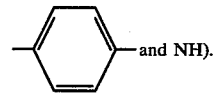 and NH).

(8) Preparation of (2S,3R)-3-amino-2-hydroxy-4-(4-methoxyphenyl)butanoyl-(S)-leucine The benzyl ester of (2S,3R)-3-benzyloxycarbonylamino-2-hydroxy-4-(4-methoxyphenyl)butanoyl-(S)-leucine (1.69 g, 3.00 mmol) was dissolved in 30 ml of 95% acetic acid. A catalytic amount of palladium black was added and hydrogen was introduced under atmospheric pressure to the solution.

When the catalytic reduction was completed at room temperature in 4.5 hours, the palladium black was separated by filtration and the filtrate was well concentrated under reduced pressure to dryness. To the residue was added 20 ml of acetone. Deposited crystals were collected by filtration and then washed with acetone and dried in vacuo. (2S,3R)-3-amino-2-hydroxy-4-(4-methoxyphenyl)butanoyl-(S)-leucine was obtained.

Yield 0.95 g (94%). Mp. 228°–231° C. (decomposition).

$[\alpha]_{578}^{31}$ −12.6° (c=1, acetic acid).

NMR Spectrum (CF$_3$COOD) δ=1.1 (d, 6H, J=5 Hz; (CH$_3$)$_2$CH), 3.3 (d, 2H, J=7 Hz; CH$_2$—Ar), 4.0 (s, 3H; CH$_3$—O), 4.1 (multi, H; C$\underline{H}$—NH$_2$), 4.7 (multi, H; C$\underline{H}$—NH) 4.8 (d, H, J=4 Hz; C$\underline{H}$—OH)

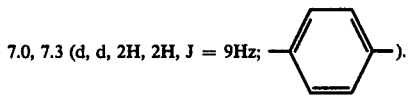

7.0, 7.3 (d, d, 2H, 2H, J = 9Hz;

EXAMPLE 2

(1) Preparation of threo-(2RS)-3-acetylamino-2-hydroxy-4-oxo-4-(2-methoxyphenyl)butanoic acid N-[2-oxo-2-(2-methoxyphenyl)ethyl]acetamide (m.p. 75°–78° C.) (16.6 g, 80.0 mmol) and 37.6 g (0.450 mol) of sodium hydrogen carbonate were dissolved in a mizture of 92.7 ml (0.450 mol) of 25% glyoxylic acid aqueous solution and 150 ml of methanol. When the reaction mixture was allowed to react at 50°–60° C., the reaction was completed after 40 hours.

The reaction solution was treated in the same manner as in Example 1 (1) and threo-(2RS)-3-acetylamino-2-hydroxy-4-oxo-4-(2-methoxyphenyl)butanoic acid was obtained.

Yield 13.2 g (58.6%).
Mp. 164°–165° C. (foaming).
NMR Spectrum (DMSO-d$_6$) δ=1.9 (s, 3H; CH$_3$—CO), 3.9 (s, 3H; CH$_3$—O), 4.5 (d, H, J=3 Hz; C$\underline{H}$—OH), 5.8 (d, d, H; C$\underline{H}$—NH),

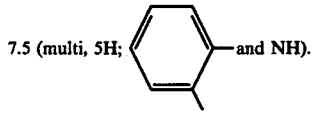

7.5 (multi, 5H; and NH).

(2) Preparation of threo-(2RS)-3-acetylamino-2-hydroxy-4-(2-methoxyphenyl)butanoic acid Threo-(2RS)-3-acetylamino-2-hydroxy-4-oxo-4-(2-methoxyphenyl)butanoic acid (1.41 g, 5.00 mmol) was dissolved in a mixture of 30 ml of acetic acid and 5 ml of methanol. When 0.3 g of 10% palladium carbon was added and hydrogen was passed at 60° C. under atmospheric pressure, the reaction was completed after about 7.5 hours.

The reaction solution was treated in the same manner as in Example 1(2) and threo-(2RS)-3-acetylamino-2-hydroxy-4-(2-methoxyphenyl)butanoic acid was obtained.

Yield 1.13 g (84.5%).
Mp. 195°–198° C. (decomposition).
NMR Spectrum (CF$_3$COOD) δ=2.3 (s, 3H; CH$_3$—CO), 3.2 (d, 2H, J=8 Hz; CH$_2$), 4.0 (s, 3H; CH$_3$—O), 4.6 (d, H, J=2 Hz; C$\underline{H}$—OH), 4.9 (multi, H; C$\underline{H}$—NH),

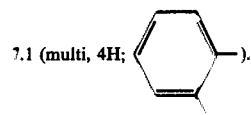

7.1 (multi, 4H;

(3) Preparation of threo-(2RS)-3-benzyloxycarbonylamino-2-hydroxy-4-(2-methoxyphenyl)butanoic acid Threo-(2RS)-3-acetylamino-2-hydroxy-4-(2-methoxyphenyl)butanoic acid (0.50 g, 1.9 mmol) was dissolved in a mixture of 3 ml of 2 N hydrochloric acid and 3 ml of dioxane. When the reaction mixture was heated at 50° C., reaction was completed after 20 hours. The reaction solution was adjusted with 5 N sodium hydroxide aqueous solution to pH 7. To the above solution were added 0.35 ml (3.7 mmol) of triethylamine and 0.77 g (2.8 mmol) of benzyl S-4,6-dimethylpyrimidin-2-iythiocarbonate in 2 ml of dioxane.

The reaction was completed through stirring overnight at room temperature. The reaction solution was treated in the same manner as in Example 1(6). Semisolid threo-(2RS)-3-benzyloxycarbonylamino-2-hydroxy-4-(2-methoxyphenyl)butanoic acid obtained.

Yield 0.42 g (63%).

(4) Preparation of threo-(2RS)-3-benzyloxycarbonylamino-2-hydroxy-4-(2-methoxyphenyl)butanoyl-(S)-leucine benzyl ester Threo-(2RS)-3-benzyloxycarbonylamino-2-hydroxy-4-(2-methoxyphenyl)butanoic acid (0.42 g, 1.2 mmol), 0.56 g (1.4 mmol) of the p-toluenesulfonic acid salt of (S)-leucine benzyl ester and 0.19 g (1.4 mmol) of 1-hydroxybenzotriazole were dissolved in 13 ml of tetrahydrofuran. While cooling in an ice-salt bath, 0.20 ml (1.4 mmol) of triethylamine and 0.24 g (1.2 mmol) of dicyclohexylcarbodiimide were added and the reaction mixture was allowed to react overnight. The reaction solution was treated in the same manner as in Example 1(7). The benzyl ester of threo-(2RS)-3-benzyloxycarbonylamino-2-hydroxy-4-(2-methoxyphenyl)butanoyl-(S)-leucine was obtained.

Yield 0.39 g (59%).
Mp. 90°–92° C.
NMR Spectrum (CDCl$_3$) δ=0.9 (d, 6H, J=4 Hz; (CH$_3$)$_2$CH), 3.0 (d, 2H, J=8 Hz; CH—CH$_2$—Ar), 3.8 (s, 3H; CH$_3$—O), 5.0, 5.1 (s, s, 2H, 2H; C$\underline{H}$$_2$—OCONH, CH$_2$—OCOCH), 5.3 (d, H, J=9 Hz; N$\underline{H}$),

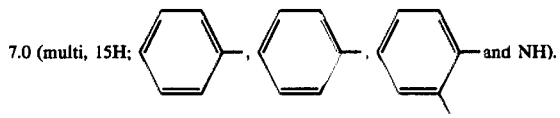

7.0 (multi, 15H; and NH).

(5) Preparation of threo-(2RS)-3-amino-2-hydroxy-4-(2-methoxyphenyl)-butanoyl-(S)-leucine The benzyl ester of threo-(2RS)-3-benzyloxycarbonylamino-2-hydroxy-4-(2-methoxyphenyl)butanoyl-(S)-leucine (0.34 g, 0.60 mmol) was dissolved in 5 ml of acetic acid, to which a catalytic amount of palladium black was added and then hydrogen was introduced under atmospheric pressure. When the reaction mixture was allowed to react at room temperature, the catalytic reduction was completed after 7 hours.

The reaction solution was treated in the same manner as in Example 1(8). Threo-(2RS)-3-amino-2-hydroxy-4-(2-methoxyphenyl)butanoyl-(S)-leucine was obtained.

Yield 118 mg (58%).
Mp. 212°–215° C. (decomposition).
$[\alpha]_{578}^{23} -12.2°$ (c=0.5, acetic acid).
NMR Spectrum (CF$_3$COOD) δ=1.1 (dd, 6H; (CH$_3$)$_2$CH), 3.3 (d, 2H, J=7 Hz; CH$_2$—Ar), 3.9 (s, 3H; CH$_3$—O), 4.2 (multi, H; CH—NH$_2$), 4.7 (d, H, J=3 Hz; CH—OH), 4.7 (multi, H; CH—NH),

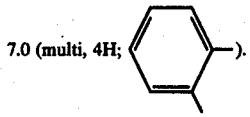
7.0 (multi, 4H;     ).

EXAMPLE 3

(1) Preparation of threo-(2RS)-3-acetylamino-2-hydroxy-4-oxo-4-(3-methoxyphenyl)butanoic acid N-[2-oxo-2-(3-methoxyphenyl)ethyl]acetamide (m.p. 104°–107° C.) (3.00 g, 14.5 mmol) and 10.2 g (0.121 mol) of sodium hydrogen carbonate were dissolved in a mixture of 20.4 ml (78.2 mmol) of 25% glyoxylic acid aqueous solution and 30 ml of methanol. When the reaction mixture was allowed to react at 50°–60° C., the reaction was completed overnight. The reaction solution was concentrated under reduced pressure and the residue was dissolved in water and then washed with ethyl acetate. The aqueous phase was separated and adjusted with hydrochloric acid to pH 1–2. Deposited oily products were extracted with ethyl acetate for three times. The extracts were combined, washed with an aqueous solution of sodium chloride and then dried over anhydrous sodium sulfate.

The sodium sulfate was separated out by filtration, and the filtrate was concentrated to dryness under reduced pressure. To the residue was added a small amount of ethyl acetate and precipitated crystals were collected by filtration, washed with ethyl acetate and then dried in vacuo. Threo-(2RS)-3-acetylamino-2-hydroxy-4-oxo-4-(3-methoxyphenyl)butanoic acid was obtained.

Yield 3.51 g (85.2%).
Mp. 159°–162° C. (decomposition).
NMR Spectrum (DMSO-d$_6$) δ=2.0 (s, 3H; CH$_3$—CO), 3.9 (s, 3H; CH$_3$—O), 4.5 (d, H, J=4 Hz; CH—OH), 5.7 (dd, H; CH—NH).

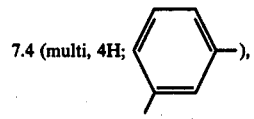
7.4 (multi, 4H;     ), 8.2 (d, H, J=9 Hz; NH).

(2) Preparation of threo-(2RS)-3-acetylamino-2-hydroxy-4-(3-methoxyphenyl)butanoic acid Threo-(2RS)-3-acetylamino-2-hydroxy-4-oxo-4-(3-methoxyphenyl)butanoic acid (1.41 g, 5.00 mmol) was dissolved in 50 ml of acetic acid, to which 1.4 g of 10% palladium carbon was added and hydrogen was introduced at 60° C. under atmospheric pressure. The reaction was completed after about 5 hours.

The reaction solution was treated in the same manner as in Example 1(2). Threo-(2RS)-3-acetylamino-2-hydroxy-4-(3-methoxyphenyl)butanoic acid was obtained.

Yield 0.81 g (61%).
Mp. 169°–172° C. (decomposition).
NMR Spectrum (CF$_3$COOD) δ=2.4 (s, 3H; CH$_3$—CO), 3.2 (d, 2H, J=8 Hz; CH$_2$), 4.1 (s, 3H; CH$_3$—O), 4.7 (d, H, J=2 Hz; CH—OH), 4.9 (multi, H; CH—NH),

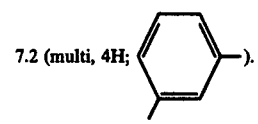
7.2 (multi, 4H;     ).

(3) Preparation of threo-(2RS)-3-benzyloxycarbonylamino-2-hydroxy-4-(3-methoxyphenyl)butanoic acid Threo-(2RS)-3-acetylamino-2-hydroxy-4-(3-methoxyphenyl)butanoic acid (0.70 g, 2.6 mmol) was dissolved in a mixture of 3 ml of 2 N hydrochloric acid and 3 ml of dioxane. When the reaction mixture was allowed to react at 50° C., the reaction was completed after 20 hours.

The reaction solution was adjusted with 5 N sodium hydroxide aqueous solution to pH 7. To the above solution were added 0.50 ml (5.2 mmol) of triethylamine and 1.08 g (3.93 mmol) of benzyl S-4,6-dimethylpyrimidin-2-ylthiocarbonate in 3 ml of dioxane.

When the reaction mixture was allowed to react under stirring at room temperature, the reaction was completed overnight. The reaction solution was treated in the same manner as in Example 1(6). Semi-solid threo-(2RS)-3-benzyloxycarbonylamino-2-hydroxy-4-(3-methoxyphenyl)butanoic acid was obtained.

Yield 0.63 g (67%).

(4) Preparation of benzyl ester of threo-(2RS)-3-benzyloxycarbonylamino-2-hydroxy-4-(3-methoxyphenyl)butanoyl-(S)-leucine Threo-(2RS)-3-benzyloxycarbonylamino-2-hydroxy-4-(3-methoxyphenyl)butanoic acid (0.63 g, 1.8 mmol), 0.84 g (2.1 mmol) of the p-toluenesulfonic acid salt of (S)-leucine benzyl ester and 0.28 g (2.1 mmol) of 1-hydroxybenzotriazole were dissolved in 20 ml of tetrahydrofuran. While cooling with a mixture of common salt and ice, 0.30 ml (2.1 mmol) of triethylamine and 0.36 g (1.8 mmol) of dicyclohexylcarbodiimide were added and the reaction mixture was allowed to react overnight. The reaction solution was treated in the same manner as in Example 1(7). The benzyl ester of threo-(2RS)-3-benzyloxycarbonylamino-2-hydroxy-4-(3-methoxyphenyl)butanoyl-(S)leucine was obtained.

Yield 0.52 g (53%).
Mp. 61°–65° C.
NMR Spectrum (CDCl$_3$) δ=0.9 (d, 6H, J=4 Hz; (CH$_3$)$_2$CH), 2.9 (d, 2H, J = 7Hz; CH CH₂—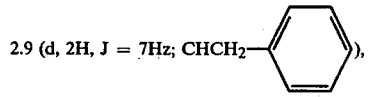), 3.7 (s, 3H; CH₃—O), 5.0, 5.1 (s, s, 2H, 2H; CH₂—O-CONH, CH₂—OCOCH), 5.5 (d, H, J=9 Hz; NH), 7.0 (multi, 15H; 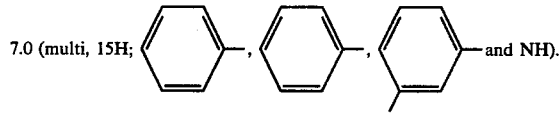 and NH).

(5) Preparation of threo-(2RS)-3-amino-2-hydroxy-4-(3-methoxyphenyl)-butanoyl-(S)-leucine The benzyl ester of threo-(2RS)-3-benzyloxycarbonylamino-2-hydroxy-4-(3-methoxyphenyl)butanoyl-(S)-leucine (0.45 g, 0.80 mmol) was dissolved in 7 ml of acetic acid, to which a catalytic amount of palladium black was added and hydrogen was introduced under atmospheric pressure. The catalytic hydrogenation was completed at room temperature after 8 hours.

The catalyst was esparated out by filtration and the filtrate was well concentrated under reduced pressure to dryness. To the residue was added 10 ml of acetone. Precipitated crystals were collected by filtration and dissolved in 1 N hydrochloric acid. Insoluble materials were filtrated off with the addition of a small amount of activated carbon and the filtrate was adjusted with aqueous ammonia to pH 5–6. Separated crystals were collected by filtration, washed with water and then acetone and dried in vacuo. Threo-(2RS)-3-amino-2-hydroxy-4-(3-methoxyphenyl)butanoyl-(S)-leucine was obtained.

Yield 137 mg (51%).
Mp. 210°–213° C. (decomposition).
[α]₅₇₈²³ −9.5° (c=0.5, acetic acid).
NMR Spectrum (CF₃COOD) δ=1.0 (dd, 6H; (CH₃)₂CH), 3.2 (multi, 2H; CH₂—Ar), 4.0 (s, 3H; CH₃—O), 4.2 (multi, H; CH—NH₂), 4.7 (multi, H; CH—NH) 4.7 (d, H, J=3 Hz; CH—OH), 7.2 (multi, 4H; 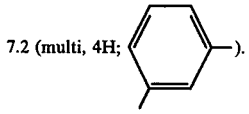).

EXAMPLE 4

(1) Preparation of threo-(2RS)-3-acetylamino-2-hydroxy-4-oxo-4-(4-phenylphenyl)butanoic acid N-[2-oxo-2-(4-phenylphenyl)ethyl]acetamide (m.p 144°–146° C.) (19.8 g, 78.0 mmol), 18.4 g (0.218 mol) of sodium hydrogen carbonate and 14.4 g (0.156 mol) of glyoxylic acid monohydrate were dissolved in a mixed solvent of 10 ml of water and 150 ml of methanol. When the solution was allowed to react at 50°–60° C., the reaction was completed overnight. The reaction solution was treated in the same manner as in Example 1(1). Threo-(2RS)-3-acetylamino-2-hydroxy-4-oxo-4-(4-phenylphenyl)butanoic acid was obtained.

Yield 25.8 g (100%).
Mp. 159°–161° C. (decomposition).
NMR Spectrum (CF₃COOD) δ=2.2 (s, 3H; CH₃), 5.1 (d, H, J=3 Hz; CH—OH), 6.2 (dd, H; CH—NH), 7.8 (multi, 9H; 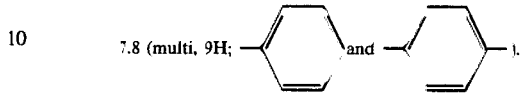).

(2) Preparation of threo-(2RS)-3-acetylamino-2-hydroxy-4-(4-phenylphenyl)butanoic acid Threo-(2RS)-3-acetylamino-2-hydroxy-4-oxo-4-(4-phenylphenyl)butanoic acid (4.91 g, 15.0 mmol) was dissolved in a mixed solvent of 135 ml of acetic acid and 30 ml of methanol and 1.0 g of 10% palladium carbon was added to the solution. When the mixture was allowed to react in the flow of hydrogen at 60° C. under atmospheric pressure, the reaction was completed after about 11 hours. The reaction mixture was treated in the same manner as in Example 1(2). Threo-(2RS)-3-acetylamino-2-hydroxy-4-(4-phenylphenyl)butanoic acid was obtained.

Yield 3.62 g (77.0%).
Mp. 175°–176° C.
NMR Spectrum (CF₃DOOD) δ=2.3 (s, 3H; CH₃), 3.1 (2H; CH₂), 4.8 (multi, 2H; CH—NH, CH—OH 7.5 (multi, 9H; 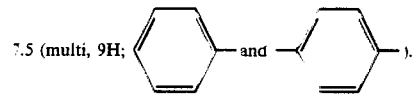).

(3) Preparation of threo-(2RS)-3-amino-2-hydroxy-4-(4-phenylphenyl)-butanoic acid Threo-(2RS)-3-acetylamino-2-hydroxy-4-(4-phenylphenyl)butanoic acid (3.13 g, 10.0 mmol) was dissolved in a mixed solvent of 12 ml of 2 N hydrochloric acid and 12 ml of dioxane. When the solution was allowed to react heated at 60° C., the reaction was completed after 24 hours. The reaction solution was decolorized by the addition of small amount of activated carbon. After separating out the activated carbon by filtration, the filtrate was adjusted with concentrated aqueous ammonia to pH 5–6. After ice cooling, deposited crystals were collected by filtration, washed with cold acetone and then dried in vacuo. Threo-(2RS)-3-amino-2-hydroxy-4-(4-phenylphenyl)butanoic acid was obtained.

Yield 2.23 g (82.2%).
Mp. 253°–257° C. (decomposition).
NMR Spectrum (CF₃COOD) δ=3.2 (2H; CH₂), 4.3 (multi, H; CH—NH₂), 4.9 (d, H, J=16 Hz, CH—OH), 7.5 (multi, 9H; 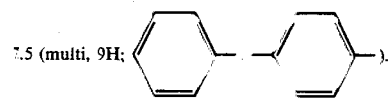).

(4) Preparation of threo-(2RS)-3-benzyloxycarbonylamino-2-hydroxy-4-(4-phenylphenyl)butanoic acid Threo-(2RS)-3-amino-2-hydroxy-4-(4-phenylphenyl)butanoic acid (1.90 g, 7.00 mmol), 1.96 ml (14.0 mmol) of triethylamine and 2.88 g (10.5 mmol) of benzyl S-4,6-dimethylprimidin-2-ylthiolcarbonate were dissolved in a mixed solvent of 7 ml of water and 10 ml of dioxane.

When the solution was allowed to react under stirring at room temperature, the reaction was completed overnight. The reaction solution was concentrated under reduced pressure. The concentrated solution was incorporated with water and then adjusted with hydrochloric acid to pH 1–2. Precipitated crystals were collected by filtration, washed with water and then with ethyl acetate successively and dried in vacuo. Threo-(2RS)-3-benzyloxycarbonylamino-2-hydroxy-4-(4-phenylphenyl)butanoic acid was obtained.

Yield 1.76 g (62.0%).
Mp. 179°–181° C.

NMR Spectrum (DMSO-$d_6$) $\delta = 2.8$ (broad, 2H; C$\underline{H}_2$—CH), 4.1 (multi, 2H; C$\underline{H}$—OH, C$\underline{H}$—NH), 5.0 (s, 2H; CH$_2$—O), 7.3 (multi, 15H; phenyl and NH).

(5) Preparation of benzyl ester of threo-(2RS)-3-benzyloxycarbonylamino-2-hydroxy-4-(4-phenylphenyl)butanoyl-(S)-leucine Threo-(2RS)-3-benzyloxycarbonylamino-2-hydroxy-4-(4-phenylphenyl)butanoic acid (1.42 g, 3.50 mmol), 1.67 g (4.20 mmol) of the p-toluenesulfonic acid salt of benzyl (S)-leucinate and 0.57 g (4.2 mmol) of 1-hydroxybenzotriazole were dissolved in 40 ml of tetrahydrofuran. While cooling with common salt and ice, were added 0.50 ml (4.2 mmol) of triethylamine and 0.72 g (3.5 mmol) of dicyclohexylcarbodiimide and they were allowed to react overnight.

The reaction mixture was treated in the same manner as in Example 1(7). The benzyl ester of threo-(2RS)-3-benzyloxycarbonylamino-2-hydroxy-4-(4-phenylphenyl)butanoyl-(S)-leucine was obtained.

Yield 1.35 g (63.4%).
Mp. 146°–149° C.

NMR Spectrum (CDCl$_3$) $\delta - 1.0$ (d, 6H, J=4 Hz; (CH$_3$)$_2$CH), 3.1 (d, 2H, J=7 Hz; CH—C$\underline{H}_2$—Ar), 5.1, 5.3 (d, s, 2H, 2H, J=2 Hz; C$\underline{H}_2$—OCOC$\underline{H}$, C$\underline{H}_2$—O-CONH), 5.5 (d, H, J=9 Hz; N$\underline{H}$), 7.5 (multi, 20H; phenyl and NH).

(6) Preparation of threo-(2RS)-3-amino-2-hydroxy-4-(4-phenylphenyl)butanoyl-(S)-leucine The benzyl ester of threo-(2RS)-3-benzyloxycarbonylamino-2-hydroxy-4-(4-phenylphenyl)butanoyl-(S)-leucine (1.22 g, 2.00 mmol) was dissolved in a mixed solvent of 15 ml of acetic acid, 15 ml of ethyl acetate and 10 ml of methanol. A catalytic amount of palladium black was added to the solution and hydrogen was introduced under atmospheric pressure. The catalytic hydrogenation was completed at room temperature after about 8 hours. The reaction mixture was treated in the same manner as in Example 1(8). Threo-(2RS)-3-amino-2-hydroxy-4-(4-phenylphenyl)butanoyl-(S)-leucine was obtained.

Yield 0.75 g (98%).
Mp. 218°–221° C. (decomposition).
$[\alpha]_{578}^{26}$ -12.9° (c=0.5, acetic acid).

NMR Spectrum (CF$_3$COOD) $\delta = 1.1$ (d, 6H, J=4 Hz; (CH$_3$)$_2$CH), 3.2 (d, 2H, J=7 Hz; CH$_2$—Ar), 4.2 (multi, H, C$\underline{H}$—NH$_2$), 4.8 (multi, H; C$\underline{H}$—NH), 5.0 (d, H, J=4 Hz; C$\underline{H}$—OH), 7.5 (multi, 9H; phenyl).

EXAMPLE 5

(1) Preparation of threo-(2RS)-3-benzoylamino-2-hydroxy-4-oxo-(4-isopropylphenyl)butanoic acid N-[2-oxo-2-(4-isopropylphenyl)ethyl]benzamide (m.p. 115°–117° C.) (3.38 g, 12.0 mmol), 2.82 g (33.6 mmol) of sodium hydrogen carbonate and 2.21 g (24.0 mmol) of glyoxylic acid monohydrate were dissolved in a mixed solvent of 20 ml of methanol, 10 ml of ethanol and 2 ml of water. When the solution was allowed to react at 50°–60° C., the reaction was completed overnight. The reaction solution was concentrated under reduced pressure to dryness. The residue was dissolved in water and washed with ethyl acetate. The aqueous phase was separated and adjusted with hydrochloric acid to pH 1–2. Deposited oily product was extracted with ethyl acetate twice. The extracts were joined, washed with water and then dried over anhydrous sodium sulfate. The sodium sulfate was separated out by filtration and the filtrate was concentrated under reduced pressure. The residue was crystallized from ether and isopropylether. Threo-(2RS)-3-benzoylamino-2-hydroxy-4-oxo-4-(4-isopropylphenyl)butanoic acid was obtained.

Yield 2.27 g (53.2%).
Mp. 153°–154° C.

NMR Spectrum (DMSO-$d_6$) $\delta = 1.3$ (d, 6H, J=7 Hz; (CH$_3$)$_2$CH), 3.0 (multi, H; (CH$_3$)$_2$C$\underline{H}$), 4.7 (d, H, J=4 Hz; C$\underline{H}$—OH), 6.0 (dd, H; C$\underline{H}$—N$\underline{H}$), 7.7 (multi, 9H; 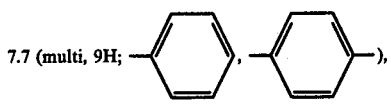), 8.4 (d, H, J=9 Hz; NH).

(2) Preparation of threo-(2RS)-3-benzoylamino-2-hydroxy-4-(4-isopropylphenyl)butanoic acid Threo-(2RS)-3-benzoylamino-2-hydroxy-4-oxo-4-(4-isopropylphenyl)butanoic acid (1.78 g, 5.00 mmol) was dissolved in 82 ml of acetic acid. When the solution was hydrogenated with additon of 0.89 g of 10% palladium carbon while introducing hydrogen at 60° C. under atmospheric pressure, the reaction was completed after about 6 hours. The catalyst was separated by filtration and the filtrate was concentrated under reduced pressure to dryness. The residue was crystallized from chloroform-petroleum ether. Threo-(2RS)-3-benzoylamino-2-hydroxy-4-(4-siopropylphenyl)butanoic acid was obtained.

Yield 1.46 g (85.5%).
Mp. 91°-94° C.
NMR Spectrum (DMSO-d$_6$) δ=1.3 (d, 6H, J=7 Hz; (CH$_3$)$_2$CH), 3.0 (d, 2H, J=7 Hz; CH$_2$), 4.1 (d, H, J=3 Hz; CH—OH), 4.6 (multi, H; CH—NH), 7.7 (multi, 10H; 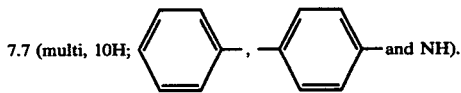 and NH).

(3) Preparation of threo-(2RS)-3-amino-2-hydroxy-4-(4-isopropylphenyl)-butanoic acid Threo-(2RS)-3-benzoylamino-2-hydroxy-4-(4-isopropylphenyl)butanoic acid (1.20 g, 3.53 mmol) was dissolved in a mixed solvent of 1 ml of 10 N hydrochloric acid and 1 ml of dioxane. When the solution was allowed to react under reflux, the reaction was completed after 6 hours. Water was added to the reaction solution which was then washed with ethyl acetate. The aqueous phase was separated and adjusted with 5 N sodium hydroxide aqueous solution to pH 5–6. Deposited crystals were collected by filtration, washed with cold water and dried in vacuo. Threo-(2RS)-3-amino-2-hydroxy-4-(4-isopropylphenyl)butanoic acid was obtained.

Yield 0.50 g (60%).

(4) Preparation of threo-(2RS)-3-benzyloxycarbonylamino-2-hydroxy-4-(4-isopropylphenyl)butanoic acid Threo-(2RS)-3-amino-2-hydroxy-4-(4-isopropylphenyl)butanoic acid (0.50 g, 2.10 mmol), 0.44 ml (3.2 mmol) of triethylamine and 0.69 g (2.5 mmol) of benzyl S-4,6-dimethylpyrimidin-2-ylthiolcarbonate were dissolved in a mixed solvent of 2.5 ml of water and 2.5 ml of dioxane. When the solution was allowed to react under stirring at room temperature, the reaction was completed overnight. The reaction solution was treated in the same manner as in Example 1(6). Threo-(2RS)-3-benzyloxycarbonylamino-2-hydroxy-4-(4-isopropylphenyl)butanoic acid was obtained.

Yield 0.43 g (55%).
Mp. 129°-130° C.
NMR Spectrum (CDCl$_3$) δ=1.3 (d, 6H, J=7 Hz; (CH$_3$)$_2$CH), 2.9 (d, 2H, J=7 Hz; CH$_2$—CH), 4.2 (d, H, J=2 Hz; CH—OH), 4.3 (multi, H; CH—NH), 5.1 (s, 2H; CH$_2$—O), 7.2 (multi, 10H; 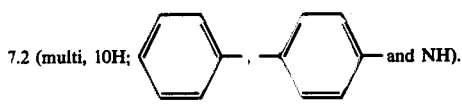 and NH).

(5) Preparation of benzyl ester of threo-(2RS)-3-benzyloxycarbonylamino-2-hydroxy-4-(4-isopropylphenyl)butanoyl-(S)-leucine Threo-(2RS)-3-benzyloxycarbonylamino-2-hydroxy-4-(4-isopropylphenyl)butanoic acid (0.37 g, 1.0 mmol), 0.48 g (1.2 mmol) of the p-toluenesulfonic acid salt of benzyl (S)-leucinate and 0.16 g (1.2 mmol) of 1-hydroxybenzotriazole were dissolved in 12 ml of tetrahydrofuran. While cooling in an ice-common salt bath, 0.17 ml (1.2 mmol) of triethylamine and 0.25 g (1.2 mmol) of dicyclohexylcarbodiimide were added. The solution was allowed to react overnight. The reaction solution was treated in the same manner as in Example 1(7). The benzyl ester of threo-(2RS)-3-benzyloxycarbonylamino-2-hydroxy-4-(4-isopropylphenyl)butanoyl-(S)-leucine was obtained.

Yield 0.51 g (88%).
Mp. 107°-110° C.
NMR Spectrum (CDCl$_3$) δ=0.9 (d, 6H, J=5 Hz; (CH$_3$)$_2$CH—CH$_2$), 1.3 (d, 6H, J=7 Hz; (CH$_3$)$_2$CH—Ar), 5.1, 5.2 (s, s, 2H, 2H; CH$_2$—OCOCH, CH$_2$—OCONH), 5.5 (d, H, J=9 Hz; NH), 7.1 (s, 4H; 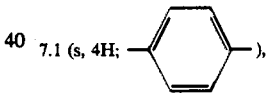), 7.3 (s, 10H; 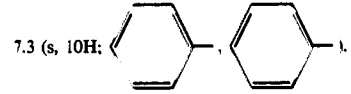).

(6) Preparation of threo-(2RS)-3-amino-2-hydroxy-4-(4-isopropylphenyl)-butanoyl-(S)-leucine The benzyl ester of threo-(2RS)-3-benzyloxycarbonylamino-2-hydroxy-4-(4-isopropylphenyl)butanoyl-(S)-leucine (0.29 g, 0.50 mmol) was dissolved in 11 ml of 90% acetic acid. A catalytic amount of palladium black was added to the solution and hydrogen was introduced under atmospheric pressure. The catalytic reduction was completed at room temperature after 7 hours. The reaction mixture was treated in the same manner as in Example 1(8). Threo-(2RS)-3-amino-2-hydroxy-4-(4-isopropylphenyl)butanoyl-(S)-leucine was obtained.

Yield 141 mg (80%).
Mp. 234°-237° C. (decomposition).
[α]$_{578}^{29}$=5.9° (c=0.5, acetic acid).
NMR Spectrum (CF$_3$COOD) δ=1.1 (d, 6H, J=6 Hz; (CH$_3$)$_2$CH—CH$_2$), 1.3 (d, 6H, J=7 Hz; (CH$_3$)$_2$CH—Ar), 3.0 (multi, 3H; CH$_2$—Ar, CH—Ar), 4.2 (multi, H; CH—NH$_2$) 4.8 (d, multi, 2H, J=3 Hz; CH—NH, CH—OH),

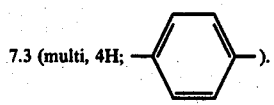

7.3 (multi, 4H;  ).

EXAMPLE 6

(1) Preparation of threo-(2RS)-3-acetylamino-2-hydroxy-4-oxo-4-(4-isopropoxyphenyl)butanoic acid N-[2-oxo-2-(4-isopropoxyphenyl)ethyl]acetamide (m.p 92°–95° C.) (1.90 g, 8.05 mmol), 1.89 g (22.5 mmol) of sodium hydrogen carbonate and 1.33 (14.5 mmol) of glyoxylic acid monohydrate were dissolved in 30 ml of methanol. When the solution was allowed to react at 50°–60° C., the reaction was completed after 6.5 hours. The reaction solution was concentrated under reduced pressure to dryness and the residue was dissolved in 30 ml of water. Insoluble compounds were separated out with ethyl acetate and the aqueous phase was adjusted with diluted hydrochloric acid to pH 1-2. Deposited oily product was extracted with 30 ml of ethyl acetate twice. The extracts were combined and dried over anhydrous sodium sulfate. The sodium sulfate was separated by filtration and the filtrate was concentrated under reduced pressure. The residue was triturated with 20 ml of ether and precipitated crystals were collected by filtration, washed with ether and dried in vacuo. Threo-(2RS)-3-acetylamino-2-hydroxy-4-oxo-4-(4-isopropoxyphenyl)butanoic acid was obtained.

Yield 1.47 g (58.8%).

Mp. 157°–158° C. (decomposition).

NMR Spectrum (DMSO-d$_6$) δ=1.3 (d, 6H, J=6 Hz; (CH$_3$)$_2$CH), 1.8 (s, 3H, CH$_3$CO), 4.4 (d, H, J=4 Hz; CH—OH), 4.7 (multi, H; (CH$_3$)$_2$CH), 5.9 (dd, H; CH—NH),

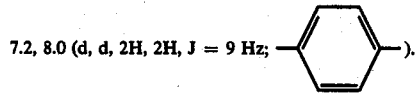

7.2, 8.0 (d, d, 2H, 2H, J = 9 Hz;  ).

(2) Preparation of threo-(2RS)-3-acetylamino-2-hydroxy-4-(4-isopropoxyphenyl)butanoic acid Threo-(2RS)-3-acetylamino-2-hydroxy-4-(4-isopropoxyphenyl)butanoic acid (1.50 g, 4.80 mmol) was dissolved in 20 ml of methanol, to which 0.2 g of 10% palladium carbon was added. When the solution was catalytically reduced in an autoclave under a hydrogen pressure of 20 Kg/cm$^2$ at 40° C. for 1 hour and then at 90° C. for 4 hours, the reaction was completed. The catalyst was separated out by filtration and the filtrate was concentrated to dryness under reduced pressure. The residue was dissolved in 20 ml of ethyl acetate and then dicyclohexylamine was added so as to adjust pH to 7, whereby crystals were deposited. Precipitated crystals were collected by filtration, washed with ethyl acetate and dried in vacuo. The dicyclohexylamine salt of threo-(2RS)-3-acetylamino-2-hydroxy-4-(4-isopropoxyphenyl)butanoic acid was obtained.

Yield 1.90 g (81.3%).

Mp. 182°–184° C.

The above acid, after removed dicyclohexylamine in the same manner as described in the succeeding Example 6(3), showed the following NMR spectrum.

NMR Spectrum (DMSO-d$_6$), δ=1.2 (d, 6H, J=6 Hz; (CH$_3$)$_2$CH), 1.8 (s, 3H, CH$_3$—CO), 2.7 (d, 2H, J=8 Hz; CH$_2$), 3.9 (d, H, J=3 Hz; CH—OH), 4.5 (multi, H; CH—NH),

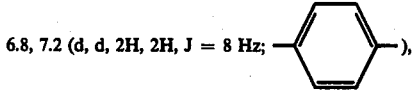

6.8, 7.2 (d, d, 2H, 2H, J = 8 Hz;  ), 7.6 (d, H, J=8 Hz; NH).

(3) Preparation of threo-(2RS)-3-benzyloxycarbonylamino-2-hydroxy-4-(4-isopropoxyphenyl)butanoic acid The dicyclohexylamine salt of threo-(2RS)-3-acetylamino-2-hydroxy-4-(4-isopropoxyphenyl)butanoic acid (1.90 g, 3.90 mmol) was added to a mixed solvent of 20 ml of N sulfuric acid and 20 ml of ethyl acetate and shaken. The ethyl acetate phase was separated, washed with water and then concentrated under reduced pressure to dryness. The residue was dissolved in a mixture of 10 ml of concentrated hydrochloric acid and 10 ml of dioxane. When the solution was heated at 70° C., the reaction was completed after 1 hour.

The reaction solution was concentrated under reduced pressure to dryness. The residue was dissolved in a mixture of 10 ml of water and 10 ml of dioxane. After adjusting pH to 8-9 by the addition of triethylamine, 1.60 g (5.90 mmol) of benzyl S-4,6-dimethylpyrimidin-2-ylthiolcarbonate was further added. When the solution was allowed to react while stirred at room temperature, the reaction was completed after two days. The reaction solution was treated in the same manner as in Example 1(6). Threo-(2RS)-3-benzyloxycarbonylamino-2-hydroxy-4-(4-isopropoxyphenyl)butanoic acid was obtained.

Yield 0.41 g (26%).

Mp. 135°–137° C.

NMR Spectrum (DMSO-d$_6$) δ=1.2 (d, 6H, J=6 Hz; (CH$_3$)$_2$CH), 2.7 (d, 2H, J=8 Hz; CH$_2$—CH), 4.0 (d, H, J=2 Hz; CH—OH), 4.5 (multi, H; CH—NH), 5.0 (s, 2H; CH$_2$—O),

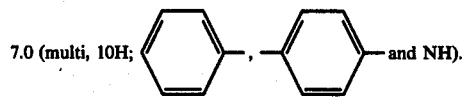

7.0 (multi, 10H;  ,  and NH).

(4) Preparation of benzyl ester of threo-(2RS)-3-benzyloxycarbonylamino-2-hydroxy-4-(4-isopropoxyphenyl)butanoyl-(S)-luecine Threo-(2RS)-3-benzyloxycarbonylamino-2-hydroxy-4-(4-isopropoxyphenyl)butanoic acid (0.40 g, 1.0 mmol), 0.44 g (1.1 mmol) of the p-toluenesulfonic acid salt of benzyl (S)-leucinate and 0.16 g (1.2 mmol) of 1-hydroxybenzotriazole were dissolved in 5 ml of tetrahydrofuran, to which 0.13 ml (1.1 mmol) of triethylamine and 0.25 g (1.2 mmol) of dicyclohexylcarbodiimide was added, while cooling with common salt and ice. The solution was allowed to react overnight. The reaction solution was treated in the same manner as in Example 1(7). The benzyl ester of threo-(2RS)-3-benzyloxycarbonylamino-2-hydroxy-4-(4-isopropoxyphenyl)butanoyl-(S)-leucine was obtained.

Yield 0.24 g (40%).

Mp. 120°-125° C.

NMR Spectrum (CDCl$_3$) $\delta$=0.9 (d, 6H, J=6 Hz; (CH$_3$)$_2$CH—CH$_2$), 1.2 (d, 6H, J=6 Hz; (CH$_3$)$_2$CH—O),2.9 (d, 2H, J=6 Hz, CH—CH$_2$—Ar), 4.1 (d, H, J=2 Hz; (CH—OH), 4.5 (multi, H; CH—NH), 5.0, 5.1 (s, s, 2H, 2H; CH$_2$—O—COCH, CH$_2$—OCONH), 5.5 (d, H, J=8 Hz; NH), 7.1 (multi, 15H; ⌬—, ⌬—, ⌬— and NH).

(5) Preparation of threo-(2RS)-3-amino-2-hydroxy-4-(4-isopropoxyphenyl)butanoyl-(S)-leucine The benzyl ester of threo-(2Rs)-3-benzyloxycarbonylamino-2-hydroxy-4-(4-isopropoxyphenyl)butanoyl-(S)-leucine (0.20 g, 0.33 mmol) was dissolved in 9 ml of 90% acetic acid. A catalytic amount of palladium black was added to the solution and hydrogen was introduced at atmospheric pressure. The catalytic reduction was completed at room temperature after 7 hours. The reaction solution was treated in the same manner as in Example 1(8). Threo-(2RS)-3-amino-2-hydroxy-4-(4-isopropoxyphenyl)butanoyl-(S)-leucine was obtained.

Yield 74 mg (59%).

Mp. 210°-215° C. (decomposition).

NMR Spectrum (CF$_3$COOD) $\delta$=1.0 (d, 6H, J=5 Hz; (CH$_3$)$_2$CH—CH$_2$), 1.4 (d, 6H, J=6 Hz; (CH$_3$)$_2$CH—O), 3.2 (d, 2H, J=6 Hz; (CH—CH$_2$—Ar), 4.2 (multi, H; (CH$_3$)$_2$CH—O), 4.7 (multi, 3H; CH—OH, CH—NH$_2$, CH—NH), 7.1, 7.3 (d, d, 2H, 2H, J = 10 Hz; —⌬—).

EXAMPLE 7

(1) Preparation of methyl ester of threo-(2RS)-3-acetylamino-2-hydroxy-4-oxo-4-(4-methoxyphenyl)butanoic acid N-[2-oxo-2-(4-methoxyphenyl)ethyl]acetamide (4.14 g, 20.0 mmol), 3.52 g (40.0 mmol) of the methyl ester of glyoxylic acid and 2.52 g (30.0 mmol) of sodium hydrogen carbonate were dissolved in a mixed solvent of 50 ml of methanol and 3 ml of water. When the solution was allowed to react at 50°-60° C., the reaction was completed overnight. The reaction solution was concentrated to dryness under reduced pressure. The residue was dissolved in 50 ml of ethyl acetate, and washed with water, a diluted aqueous solution of sodium hydrogen sulfite and then water successively. The ethyl acetate phase was separated and dried over anhydrous sodium sulfate. The sodium sulfate was separated out by filtration and the filtrate was concentrated under reduced pressure. Oily product obtained was subjected to silica gel column chromatography using chloroform-methanol (9:1 v/v) as a solvent. Fractions containing the aimed product were collected and concentrated under reduced pressure. The methyl ester of threo-(2RS)-3-acetylamino-2-hydroxy-4-oxo-4-(4-methoxyphenyl)butanoic acid was obtained.

Yield 2.67 g (45.3%).

Mp. 148°-151° C.

NMR Spectrum (DMSO-d$_6$) $\delta$=1.9 (s, 3H, CH$_3$—CO), 3.6, 3.9 (s, s, 3H, 3H, CH$_3$—OCO, CH$_3$—OAr), 4.5 (d, H, J=4 Hz; CH—OH), 5.7 (dd, H; CH—NH), 7.1, 7.9 (d, d, 2H, 2H, J = 9 Hz; —⌬—), 8.2 (d, H, J=9 Hz; NH).

(2) Preparation of methyl ester of threo-(2RS)-3-acetylamino-2-hydroxy-4-(4-methoxyphenyl)butanoic acid The methyl ester of threo-(2RS)-3-acetylamino-2-hydroxy-4-oxo-4-(4-methoxyphenyl)butanoic acid (2.00 g, 6.78 mmol) was dissolved in 50 ml of methanol, to which 0.20 g of 10% palladium carbon was added. When the solution was reduced in an autoclave under a hydrogen pressure of 30 kg/cm$^2$ at 40° C. for 1 hour and then at 80°-90° C. for 5 hours, the reaction was completed. The catalyst was separated out by filtration and the filtrate was concentrated to dryness under reduced pressure. Crystals deposited from ether were collected by filtration, washed with ether and dried in vacuo. The methyl ester of threo-(2RS)-3-acetylamino-2-hydroxy-4-(4-methoxyphenyl)butanoic acid was obtained.

Yield 1.62 g (85.0%).

Mp. 105°-110° C.

NMR Spectrum (DMSO-d$_6$) $\delta$=1.8 (s, 3H, CH$_3$—CO), 2.8 (d, 2H, J=7 Hz; CH$_2$), 3.6, 3.7 (s, s, 3H, 3H; CH$_3$—OCO, CH$_3$—OAr), 4.1 (d, H, J=2Hz; CH—OH), 4.3 (multi, H; CH—NH), 6.8, 7.2 (d, d, 2H, 2H, J = 9Hz; —⌬—), 7.4 (d, H, J=9 Hz; NH).

Other compounds listed in Table 2 were also prepared in analogous procedures to those in the foregoing examples. As the starting compounds of formula (III), those corresponding compounds represented by the formula (I) or (II) were employed. All of the compounds are of threo-(2RS) form unless otherwise referred to for their optical isomeric form.

TABLE 2

Compounds and physical properties thereof

| Example No. | The compounds of the formula (III) $$R_1-\underset{\underset{O}{\|}}{C}-\underset{\underset{R_2}{\|}}{CH}-\underset{\underset{OH}{\|}}{CH}-COOR_3$$ | The compounds of the formula (IV) $$R_1-CH_2-\underset{\underset{R_2}{\|}}{CH}-\underset{\underset{OH}{\|}}{CH}-COOR_3$$ |
|---|---|---|
| 8 | $R_1$ = 4-isobutylphenyl, $R_2$ = benzoylamino<br>$R_3$ = hydrogen<br>m.p. 155–158° C. (decomposition)<br>NMR Spectrum (DMSO-$d_6$)<br>$\delta$ = 0.9(d,6H, J = 7Hz; (CH$_3$)$_2$CH),<br>1.9(multi, H; (CH$_3$)$_2$CH), 2.6(d,2H,J = 7Hz; CH$_2$), 4.7(d,h,J = 3Hz; CH—OH),<br>6.0(dd,H; CH—NH), 7.7(multi, 9H; —⟨⟩,<br>—⟨⟩—), 8.4(d,H,J = 9Hz; NH). | $R_1$ = 4-isobutylphenyl, $R_2$ = benzoylamino<br>$R_3$ = hydrogen<br>m.p. 127–130° C.<br>NMR Spectrum (DMSO-$d_6$) $\delta$ = 0.9(d, 6H, J = 7Hz; (CH$_3$)$_3$CH), 1.8 (multi, H; (CH$_3$)$_2$CH), 2.4(d,2H,J = 7Hz; (CH$_3$)$_2$CH—CH$_2$) 3.0(d,H,J = 8Hz; CH$_2$CHCH),<br>4.1(d,H,J = 3Hz; CH—OH), 4.6(multi, H;<br>CH—NH), 7.6(multi, 10H; —⟨⟩—, —⟨⟩—<br>and NH). |
| 9 | $R_1$ = 4-isobutoxyphenyl, $R_2$ = acetylamino<br>$R_3$ = hydrogen<br>m.p. 125–127° C. (foaming)<br>NMR Spectrum (DMSO-$d_6$)<br>$\delta$ = 1.0(d,6H,J = 7Hz; (CH$_3$)$_2$CH),<br>1.9 (s,3H; CH$_3$—CO), 3.8(d,2H,J = 6Hz; CH$_2$),<br>4.4(d,H,J = 4Hz; CH—OH), 5.8(dd,H; CH—NH),<br>7.1, 7.9(d,d,2H,2H,J = 8Hz; —⟨⟩—),<br>8.0(d,H,J = 8Hz; NH) | $R_1$ = 4-isobutoxyphenyl, $R_2$ = acetylamino<br>$R_3$ = hydrogen<br>m.p. 135–140° C. |
| 10 | $R_1$ = 4-fluorophenyl, $R_2$ = acetylamino<br>$R_3$ = hydrogen<br>m.p. 152–154° C.<br>NMR Spectrum (DMSO-$d_6$) $\delta$ = 1.9(s,3H; CH$_3$)<br>4.4(d,H,J = 4Hz; CH—OH), 5.6(dd,H; CH—NH)<br>27(multi, 5H; —⟨⟩—and NH) | $R_1$ = 4-fluorophenyl, $R_2$ = acetylamino<br>$R_3$ = hydrogen<br>m.p. 190–191° C.<br>NMR Spectrum (CF$_3$COOD) $\delta$ = 2.3(s,3H; CH$_3$),<br>3.1(d,2H,J = 8Hz; CH$_2$), 4.6(d,6(d,H,J = 3Hz;<br>CH—OH), 4.9(multi, H; CH—NH),<br>7.2(multi, 4H; —⟨⟩—). |
| 11 | $R_1$ = 3-hydroxyphenyl, $R_2$ = acetylamino,<br>$R_3$ = hydrogen<br>m.p. 184–187° C. (decomposition)<br>NMR Spectrum (DMSO-$d_6$) $\delta$ = 1.9(s,3H; CH$_3$)<br>4.5(d,H,J = 3Hz; CH—OH), 5.7(dd,H; CH—NH)<br>7.2(multi, 4H; ⟨⟩—), 8.0(d,H,J = 9Hz; NH) | $R_1$ = 3-hydroxyphenyl, $R_2$ = acetylamino,<br>$R_3$ = hydrogen<br>m.p. 182–191° C. (decomposition)<br>NMR Spectrum (CF$_3$COOD) $\delta$ = 2.3(s,3H; CH$_3$),<br>3.1(d,2H,J = 7Hz; CH$_2$), 4.7(d,H,J = 2Hz;<br>CH—OH), 4.9(multi, H; CH—NH),<br>7.1(multi, 4H; ⟨⟩—). |
| 12 | $R_1$ = 1-naphthyl, $R_2$ = aetylamino,<br>$R_3$ = hydrogen<br>m.p. 162–163° C. (decomposition)<br>NMR Spectrum (DMSO-$d_6$), $\delta$ = 2.0(s,3H; CH$_3$)<br>4.5(d,H,J = 4Hz; CH—OH), 5.8(dd,H; CH—NH)<br>29(multi, 8H; ⟨naphthyl⟩ and NH). | $R_1$ = 1-naphthyl, $R_2$ = acetylamino,<br>$R_3$ = hydrogen<br>m.p. 164–168° C.<br>NMR Spectrum (DMSO-$d_6$), $\delta$ = 1.8(s,3H; CH$_3$), 3.2(d,2H,J = 7Hz; CH$_2$)<br>3.9(d,H,J = 3Hz; CH—OH),<br>4.3(multi, H; CH—NH), |

TABLE 2-continued

Compounds and physical properties thereof

| Example No. | | |
|---|---|---|
| 13 | $R_1$ = 2-naphthyl, $R_2$ = acetylamino, $R_3$ = hydrogen<br>m.p. 138.5–141.5° C.(decomposition)<br>NMR Spectrum (DMSO-$d_6$)<br>$\delta$ = 2.0(s,3H; $CH_3$), 4.6(d,H,J = 4Hz; CH—OH),<br><br>5.9(dd,H;CH—NH), 8.2(multi, 8H; 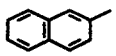)<br><br>and NH). | 7.5(s, multi, 7H; )<br>8.3(d,H,J = 8Hz; NH).<br>$R_1$ = 2-naphthyl, $R_2$ = acetylamino, $R_3$ = ]hydrogen<br>m.p. 174–178° C.)<br>NMR Spectrum ($CF_3COOD$) $\delta$ = 2.2(s,3H; $CH_3$)<br>3.2(d,2H,J = 8Hz; $CH_2$), 4.6(d,H,J = 3Hz;<br><br>CH—OH), 5.0(multi, H; CH—NH),<br><br>7.6(multi, 7H; ). |
| 14 | $R_1$ = 2-methoxyphenyl, $R_2$ = acetylamino<br>$R_3$ = hydrogen<br>See Example 2-(1) | $R_1$ = 2-methoxyphenyl, $R_2$ = acetylamino<br>$R_3$ = hydrogen<br>See Example 2-(2) |
| 15 | $R_1$ = 3,4-dihydroxyphenyl, $R_2$ = acetylamino<br>$R_3$ = hydrogen<br>m.p. 146–150° C. (decomposition)<br>NMR Spectrum (DMSO-$d_6$) $\delta$ = 1.9(s,3H; $CH_3$)<br>4.4(d,H,J = 4Hz; CH—OH), 5.6(dd,H; CH—NH),<br><br>7.2 (multi, 3H; ),<br><br>7.9(d,H,J = 9Hz; NH). | $R_1$ = 3,4-dihydroxyphenyl,<br>$R_2$ = acetylamino, $R_3$ = hydrogen<br>m.p. 235–239° C. (decomposition)<br>NMR Spectrum ($CF_3COOD$) $\delta$ = 2.3(s; $CH_3$),<br>4.7, 4.8(d, multi, H,H; CH—OH, CH—NH),<br><br>7.9(multi, 3H; ). |

| | | |
|---|---|---|
| | The compounds of the formula (V) | $R_1$—$CH_2$—CH—CH—COOH with OH and $R_2'$ substituents 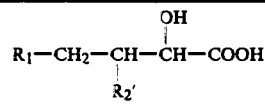 |

| | | |
|---|---|---|
| 8 | $R_1$ = 4-isobutylphenyl, $R_2'$ = amino<br>m.p. 240–245° C. (decomposition) | $R_1$ = 4-isobutylphenyl, $R'_2$ = benzyloxy-<br>carbonylamino<br>m.p. 155–160° C.<br>NMR Spectrum (DMSO-$d_6$)<br>$\delta$ = 0.9(d,6H,J = 7Hz; $(CH_3)_2CH$),<br>1.8(multi, H; $(CH_3)_2CH$),<br>2.4(d,2H,J = 7Hz; $(CH_3)_2CHCH_2$),<br>2.8(d,2H,J = 6Hz; $CH_2CHCH$), 4.1(multi, 2H;<br>CH—OH, CH—NH), 4.9(d,2H,J = 3Hz; $CH_2$—O),<br><br>7.2(multi, 10H; , and NH). |
| 9 | | $R_1$ = 4-isobutoxyphenyl,<br>$R_2'$ = benzyloxycarbonylamino<br>m.p. 172–180° C. |
| 10 | $R_1$ = 4-fluorophenyl,<br>$R_2'$ = benzyloxycarbonylamino<br>m.p. 126–132° C.<br>NMR Spectrum (DMSO-$d_6$)<br>$\delta$ = 2.8(d,2H,J = 6Hz; $CH_2$—CH),<br>4.0(multi, 2H; CH—NH, CH—OH),<br><br>4.9(s,2H; $CH_2$—O), 7.1(multi, 10H; ,<br><br>and NH). | |
| 11 | $R_1$ = 3-hydroxyphenyl,<br>$R_2'$ = benzyloxycarbonylamino<br>m.p. 120–125° C.<br>NMR Spectrum (DMSO-$d_6$)<br>$\delta$ = 2.7(d,2H,J = 7Hz; $CH_2$—CH),<br>4.0(d,H,J = 3Hz; CH—OH),<br>4.1(multi, H; CH—NH), 5.0(s,2H; $CH_2$—O), | |

TABLE 2-continued

Compounds and physical properties thereof

| Example No. | | |
|---|---|---|
| | 7.0(multi, 11H; 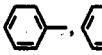, 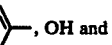, OH and NH). | |
| 12 | R₁ = 1-naphthyl, R₂' = amino<br>m.p. 214–215° C. (decomposition)<br>NMR Spectrum (CF₃COOD)<br>δ = 3.5(d,2H,J = 8Hz; CH₂),<br>4.2 (multi, H; CH—NH₂);<br><br>4.7(d,H,J = 4Hz; CH—OH), 7.5(multi, 7H; 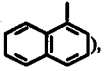), | R₁ = 1-naphthyl, R₂' = benzyloxycarbonylamino<br>m.p. 110–120° C.<br>NMR Spectrum (CDCl₃)<br>δ = 2.8(d,2H,J = 8Hz; CH₂—CH)<br>4.1(d,H,J = 2Hz; CH—OH),<br><br>4.4(multi, H; CH—NH), 5.0(s,2H; CH₂—O),<br><br>7.3(multi, 12H; 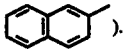—and 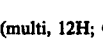),<br><br>8.3(d,H,J = 9Hz; NH). |
| 13 | R₁ = 2-naphthyl, R₂' = amino<br>NMR Spectrum (CF₃COOD)<br>δ = 3.4(dd,2H; CH₂), 4.3(multi, H; CH—NH),<br>4.7(d,H,J = 3Hz; CH—OH),<br><br>7.6(multi, 7H; 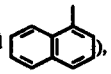). | R₁ = 2-naphthyl, R₂' = benzyloxycarbonylamino<br>m.p. 172–174° C.<br>NMR Spectrum (DMSO-d₆)<br>δ = 3.0(d,2H,H = 8Hz; CH₂—CH),<br><br>4.0(d,H,J = 3Hz; CH—OH),<br><br>4.2(multi, H; CH—NH), 4.9(s,2H; CH₂—O),<br><br>7.4(multi, 13H; 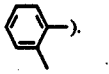, —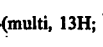—and NH). |
| 14 | R₁ = 2-hydroxyphenyl, R₂' = amino<br>(*See Note 1)<br>m.p. 235–239° C.<br>NMR Spectrum (CF₃COOD)<br>δ = 3.4(d,2H,J = 7Hz; CH₂), 4.3(multi, H;<br>CH—NH), 4.7(d,H,J = 4Hz; CH—OH),<br><br>7.2(multi, 4H; 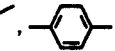). | R₁ = 2-hydroxyphenyl,<br>R₂' = benzyloxycarbonylamino<br>m.p. 110–115° C.<br>NMR Spectrum (CDCl₃)<br>δ = 2.9(d,2H,J = 7Hz; CH₂—CH),<br>4.2(d,H,J = 2Hz; CH—OH), 4.3(multi,H;<br><br>6.9(multi, 11H; —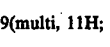—, ——, OH and<br><br>NH). |
| 15 | A NMR Spectrum (DMSO-d₆) δ = 2.8(d,2H,J = 8Hz; CH₂—CH),<br>4.1, 4.2(d, multi, H,H,J = 2Hz; CH—OH, CH—NH), 5.0 (s,2H; CH₂—O),<br><br>6.7(multi, 3H; —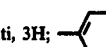—), 7.2(s,5H; 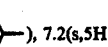—).<br><br>B m.p. 129–133° C.<br><br>NMR (DMSO-d₆) δ = 4.9(s,CH₂; CH₂—O), 6.5(multi, 3H; —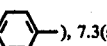—), 7.3(s,5H; 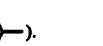—). | |

*See Note 2

| The compound of the formula (VII') | The compound of the formula (VII) |
|---|---|
| $$R_1-CH_2-\underset{R_2''}{\overset{OH}{\underset{|}{CH}}}-\underset{|}{CH}-CONH\underset{R_4}{\overset{|}{CH}}-P \quad \begin{array}{l} R'' = \text{protected amino} \\ P = \text{protected carbonyl} \end{array}$$ | $$R_1-CH_2-\underset{NH_2}{\overset{OH}{\underset{|}{CH}}}-CH-CONHCHOOH \atop R_4$$ |

[Intermediate of the compound of the formula (VII)]

| | | |
|---|---|---|
| 8 | R₁ = 4-isobutylphenyl, R₂″ = benzyloxycarbonyl-<br>amino, R₄ = isobutyl, p = benzyloxycarbonyl<br>m.p. 110–113° C.<br>NMR Spectrum (CDCl₃)<br>δ = 0.9(d,6H,J = 7Hz; (CH₃)₂CHCH₂—Ar),<br>0.9(d,6H,J = 7Hz; (CH₃)₂CHCH₂CH)<br>2.4(d,2H,J = 7Hz; (CH₃)₂CHCH₂—Ar),<br>2.9(multi, 2H; CHCHCH₂—Ar),<br>5.0, 5.1(s,s,2H,2H; CH₂—OCOCH,<br>CH₂—OCONH), 5.3(d,H,J = 9Hz; NH), | R₁ = 4-isobutylphenyl, R₄ = isobutyl<br><br>m.p. 221–226° C.,<br>[α]₅₇₈²⁹ − 10.1° (c = 0.5, acetic acid)<br>NMR Spectrum (CF₃COOD)<br>δ = 0.9(d,6H,J = 7Hz; (CH₃)₂CHCH₂),<br>1.1(d,6H,J = 7Hz; (CH₃)₂CHCH₂),<br>2.5(d,2H,J = 7Hz; (CH₃)₂CHCH₂—Ar),<br>3.2(multi, 2H, CHCHCH₂—Ar),<br>4.2(multi, H; CH—NH₂), 4.8(multi, H; |

TABLE 2-continued

Compounds and physical properties thereof

| Example No. | | |
|---|---|---|
| 9 | 7.3(multi, H; , , and NH).<br><br>$R_1$ = 4-isobutoxyphenyl, $R_2''$ = benzyloxycarbonylamino, $R_4$ = isobutyl, p = benzyloxycarbonyl<br>m.p. 131–136° C. | CH—NH), 5.0(d,H,J = 4Hz; CH—OH),<br><br>7.2(s,4H; ).<br><br>$R_1$ = 4-isobutylophenyl, $R_4$ = isobutyl<br>m.p. 210–215° C. |
| 10 | $R_1$ = 4-fluorophenyl,<br>$R_2''$ = benzyloxycarbonylamino,<br>$R_4$ = isobutyl, P = benzyloxycarbonyl<br>m.p. 94–101° C.<br>NMR Spectrum (CDCl$_3$)<br>δ = 0.8(d,6H; (CH$_3$)$_2$CH), 2.9(d,2H,7Hz;<br><br>CH—CH$_2$—), 4.9, 5.1(s,s,2H,2H;<br><br>CH$_2$—OCOCH, CH$_2$—OCONH),<br><br>5.6(d,H,J = 9Hz; NH),<br><br>7.2(multi, 15H; , , , NH). | $R_1$ = 4-fluorophenyl, $R_4$ = isobutyl<br><br>m.p. 220–225° C. (decomposition),<br>$[α]_{578}^{27}$ − 4.0° (c = 0.9, acetic acid)<br>NMR Spectrum (CF$_3$COOD) δ = 1.0(dd,6H; (CH$_3$)$_2$CH),<br><br>3.2(d,2H,J = 6Hz; CH$_2$—Ar), 4.2(multi, H; CH—NH$_2$),<br><br>4.8(multi, 2H; CH—NH, CH—OH),<br><br>7.1 (multi, 4H; ). |
| 11 | $R_1$ = 3-hydroxyphenyl,<br>$R_2''$ = benzyloxycarbonylamino,<br>$R_4$ = isobutyl, P = benzyloxycarbonyl<br>m.p. 141–145° C.<br>NMR Spectrum (CDCl$_3$)<br>δ = 0.8(d,6H,J = 5Hz; (CH$_3$)$_2$CH),<br><br>2.8(d,2H,J = 7Hz; CHCH$_2$—Ar),<br>5.0, 5.1(s,s2H,2H; CH$_2$—OCOCH, CH$_2$—OCONH),<br>5.5(d,H, J = 9Hz; NH),<br><br>7.1(multi, 16H; , , ,) OH and NH). | $R_1$ = 3-hydroxyphenyl, $R_4$ = isobutyl<br><br><br>NMR Spectrum (CF$_3$COOD)<br>δ = 1.1(dd,6H; (CH$_3$)$_2$CH),<br>3.3(d,2H, J = 6Hz; CH$_2$—Ar), 4.2(multi, H; CH—NH$_2$),<br><br>4.8(multi, 2H; CH—OH, CH—NH), 7.1(multi, 4H; ). |
| 12 | $R_1$ = 1-naphthyl,<br>$R_2''$ = benzyloxycarbonylamino<br>$R_4$ = isobutyl, P = benzyloxycarbonyl<br>m.p. 124–128° C.<br>NMR Spectrum (CDCl$_3$)<br>δ = 0.9(d,6H,J = 4Hz; (CH$_3$)$_2$CH),<br><br>2.8(d,2H,J = 7Hz; CH$_2$—), 5.0, 5.1(s,s,2H, 2H; CH$_2$—OCONH, CH$_2$—OCOCH),<br><br>5.7(d,2H,J = 9Hz; NH), 7.4(multi, 18H; ),<br><br>, and NH). | $R_1$ = 1-naphthyl, $R_4$ = isobutyl<br><br>m.p. 185–191° C. (decomposition) |
| 13 | $R_1$ = 2-naphthyl,<br>$R_2''$ = benzyloxycarbonylamino,<br>$R_4$ = isobutyl, P = benzyloxycarbonyl<br>m.p. 119–122° C.<br>NMR Spectrum (CDCl$_3$) δ = 0.9(dd,6H; (CH$_3$)CH), | $R_1$ = 2-naphthyl, $R_4$ = isobutyl<br><br>m.p. 226–229° C. (decomposition)<br>$[α]_{578}^{25}$ − 6.5° (c = 1, acetic acid). |

TABLE 2-continued
Compounds and physical properties thereof

| Example No. | | |
|---|---|---|
| | 3.1(d,2H,J = 7Hz; CH$_2$—), 5.0, 5.1(s,s,2H,2H; CH$_2$—OCOCH, CH$_2$—OCONH), 5.5(d,H,J = 8Hz; NH), 7.4(multi, 18H; 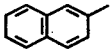, 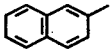 and NH). | NMR Spectrum (CF$_3$COOD) δ = 1.0(dd,6H; (CH$_3$)$_2$CH), 3.4(multi, 2H; CH$_2$—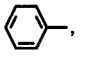), 4.3(multi, H; CH—NH$_2$), 4.8(multi, 2H; CH—OH, CH—NH), 7.6(multi, 7H; 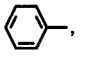). |
| 14 | R$_1$ = 2-hydroxyphenyl, R$_2''$ = benzyloxycarbonylamino R$_4$ = isobutyl, P = benzyloxycarbonyl m.p. 120-130° C. NMR Spectrum (CDCl$_3$) δ = 0.9(d,6H,J = 5Hz; (CH$_3$)$_2$CH) 3.0(d,2H,J = 8Hz; CHCH$_2$—Ar). 5.0, 5.1(s,s,2H,2H; CH$_2$—OCOCH, CH$_2$—OCONH), 5.3(d,h,J = 9Hz; NH), 7.1(multi, 16H; 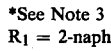, , , OH and NH). | R$_1$ = 2-hydroxyphenyl, R$_4$ = isobutyl m.p. 238-14 244° C. (decomposition) [α]$_{578}^{29}$ − 7.7° (c = 0.5, acetic acid) NMR Spectrum (CF$_3$COOD) δ = 1.1(dd,6H; (CH$_3$)$_2$CH), 3.2(d,2H,J = 7Hz; CH$_2$—Ar), 4.3(multi, H; CH—NH$_2$), 4.7(multi, 2H; CH—OH, CH—NH), 7.1 (multi, 4H; 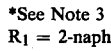). |
| 15 | R$_1$ = 3,4-dihydroxyphenyl, R$_2''$ = benzyloxycarbonyl m.p. 70-75° C. NMR Spectrum (CDCl$_3$) δ = 0.8(d,6H; J = 4Hz; (CH$_3$)$_2$CH). | R$_1$ = 3,4-dihydroxyphenyl, R$_4$ = isobutyl m.p. 175-185° C. (decomposition) [α]$_{578}^{29}$ − 13.3° (c = 0.5, acetic acid) NMR Spectrum (CF$_3$COOD) δ = 1.1(dd,6H; (CH$_3$)$_2$CH), 3.2(d,H,J = 6Hz; CH$_2$—Ar), 4.2(multi, H; CH—NH$_2$), 4.9(multi, 2H; CH—OH, CH—NH), 7.1(multi, 3H; ). |
| 16 | R$_1$ = 4-methoxyphenyl, R$_2''$ = benzyloxycarbonylamino R$_4$ = isopropyl, P = benzyloxycarbonyl, (2S,3R)-Form m.p. 123-125° C. [α]$_{578}^{28}$ + 22.8° (c = 1, acetic acid) NMR Spectrum (CDCl$_3$) δ = 0.8 (dd,6H; (CH$_3$)$_2$CH), 2.1(multi, H; (CH$_3$)$_2$CH), 2.9(d,2H,J = 7Hz; CH—CH$_2$—Ar), 3.9(s,3H; CH$_3$—O), 4.2(dd, multi, H,H; CH—OH, CH$_2$—CH—NH) 4.6(dd, H; CO—CH—NH), 5.0, 5.1(s,s,2H,2H; CH$_2$—OCOCH, CH$_2$—OCONH), 5.9(d,H,J = 8Hz; NH), 6.7, 7.1(d,d,2H,2H,J = 8Hz; ), 7.2, 7.3(s,s,5H,5H; , 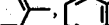). | R$_1$ = 4-methoxyphenyl, R$_4$ = isopropyl (2S,3R)-Form m.p. 240-243° C. (decomposition) [α]$_{578}^{31}$ + 5.0° (c = 1, acetic acid) NMR Spectrum (CF$_3$COOD) δ = 1.1 (d,6H,J = 7Hz; (CH$_3$)$_2$CH), 2.4(multi, H; (CH$_3$)$_2$CH) 3.3(multi, 2H; CH$_2$—Ar). 4.0(s,3H; CH$_3$—O) 4.1(multi, H; CH—NH$_2$), 4.6(d,H,J = 6Hz; CH—NH), 4.9(d,H,J = 3Hz; CH—OH), 7.1, 7.3(d,d,2H,2H,J = 9Hz; 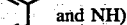). |
| | *See Note 3 | |
| 17 | R$_1$ = 2-naphthyl, R$_2''$ = benzyloxycarbonylamino, R$_4$ = 1-methylpropyl, P = benzyloxycarbonyl m.p. 106-111° C. NMR Spectrum (CDCl$_3$) δ = 0.8, 0.9(d,t,3H,3H,J = 6Hz; CH$_3$—CH, CH$_3$—CH$_2$), 3.1(d,2H,j = 7Hz; CH—CH$_2$—Ar), 4.2(d,H,J = 2Hz; CH—OH), 4.6(multi, H; CH—NH), 4.9, 5.1(s,s,2H,2H; CH$_2$—OCOCH, CH$_2$—OCONH), 5.7(d,h,J = 8Hz; NH), 7.5(multi, 18H; 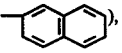, 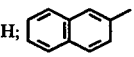, 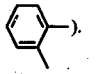 and NH). | R$_1$ = 2-naphthyl R$_4$ = 1-methylpropyl m.p. 225-230° C. (decomposition) [α]$_{578}^{31}$ + 17.3° (c = 1, acetic acid) NMR Spectrum (CF$_3$COOD) δ = 1.1(d,t,3H,3H;CH$_3$—CH, CH$_3$—CH$_2$), 3.4(d,2H,J = 6Hz; CH$_2$—Ar), 4.3(multi, H; CH—NH$_2$), 4.7(d,H,J = 5Hz; CH—NH), 4.9(d,H,J = 4Hz; CH—OH), 7.6(multi, 7H; 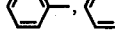). |

TABLE 2-continued

Compounds and physical properties thereof

Example
No.

*See Note 4

Note 1:
Preparation of threo-(2RS)-3-amino-2-hydroxy-4-(2-hydroxyphenyl)butanoic acid
Threo-(2RS)-3-acetylamino-2-hydroxy-4-(2-methoxyphenyl) butanoic acid (2.67 g, 10.0 mmol) prepared in Example 2(2) was added to 12 ml of 47% hydrobromic acid. When the mixture was heated at 100° C., the reaction was completed after 6 hours. The reaction mixture was concentrated to dryness under reduced pressure. The residue was dissolved in 10 ml of water and concentrated under reduced pressure to dryness. The above dissolving and concentrating procedure was repeated once again. Finally, the residue was dissolved in 10 ml of water and the aqueous phase was adjusted with concentrated aqueous ammonia to pH 5–6. After ice cooling, deposited crystals were collected by filtration, washed with cold water and in vacuo. Threo-(2RS)-3-amino-2-hydroxy-4-(2-hydroxyphenyl)butanoic acid was obtained (1.40 g).
Note 2:
Threo-(2RS)-3-benzyloxycarbonylamino-2-hydroxy-4-(3,4-dihydroxyphenyl)butanoic acid prepared by reaction of threo-(2RS)-3-acetylamino-2-hydroxy-4-(3,4-dihydroxyphenyl)butanoic acid and benzyl S—4,6-dimethylpyridin-2-ylthiocarbonate was isolated in the same manner as the isolation of the reaction product in Example 1(6). The isolated compound was hydroscopic. NMR spectrums of the isolated compound are shown in the column A of Table.
A portion of the crystals was dissolved in acetone and the solution was neutralized by the addition of dicyclohexylamine. Deposited crystals were collected by filtration, washed with acetone and dried in vacuo. Melting point and NMR spectrums of the dicyclohexylamine salt prepared are shown in the column B of the Table.Note 3:
The starting material used here was (2S,3R)-3-benzyloxycarbonylamino-2-hydroxy-4-(4-methoxyphenyl)butanoic acid prepared in Example 1(6).
Note 4:
The starting material herewas threo-(2RS)-3-benzyloxycarbonylamino-2-hydroxy-4-(2-naphthyl)butanoic acid, the compound of the formula (V), prepared in Example 12.
Note 5:
The physical properties of the following compounds, which is used as materials in Examples 8 and 10, are as follows; N—[2-oxo-2-)4-isobutylphenyl)ethyl]benzamide: m.p. 106–109° C. N—[2-oxo-2-(4-fluorophenyl)ethyl]acetamide: m.p. 153–155° C.

EXAMPLE 18

(1) Preparation of threo-(2RS)-3-acetylamino-2-hydroxy-4-oxo-4-(4-bromophenyl)butanoic acid N-[2-oxo-2-(4-bromophenyl)ethyl]acetamide (m.p. 173°–175° C.) (17.0 g, 66.0 mmol), 15.8 g (0.188 mol) of sodium hydrogen carbonate and 10.9 g (0.120 mol) of glyoxylic acid monohydrate were dissolved in a mixed solvent of 170 ml of methanol and 20 ml of water. When the solution was allowed to react at 50°–60° C., the reaction was completed after 5 hours. The reaction solution was treated in the same manner as in Example 1(1). Threo-(2RS)-3-acetylamino-2-hydroxy-4-oxo-4-(4-bromophenyl)butanoic acid was obtained.

Yield 12.7 g (58.4%).
Mp. 177°–180° C. (decomposition).
NMR Spectrum (DMSO-$d_6$) $\delta = 1.8$ (s, 3H; $CH_3$), 4.5 (d, H, J=5 Hz; C$\underline{H}$—OH), 5.6 (dd, H; C$\underline{H}$—NH),

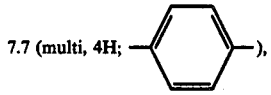

7.7 (multi, 4H;

8.1 (d, H, J=8 Hz; NH).

EXAMPLE 19

(1) Preparation of threo-(2RS)-3-acetylamino-2-hydroxy-4-oxo-4-phenyl-butanoic acid N-(2-oxo-2-phenylethyl)acetamide (4.43 g, 0.025 mol) and 4.20 g (0.05 mol) of sodium hydrogen carbonate were dissolved in a mixed solvent of 13.0 g (0.044 mol) of 25% glyoxylic acid aqueous solution and 25 ml of water. When the solution was allowed to react at 50°–60° C., the reaction was completed overnight. The reaction solution was cooled with ice and adjusted with diluted hydrochloric acid to pH 1–2. Deposited crystals were collected by filtration, washed with water and dried in vacuo over phosphorous pentoxide.

Threo-(2RS)-3-acetylamino-2-hydroxy-4-oxo-4-phenylbutanoic acid was obtained.
Yield 4.07 g (64.9%).
Mp. 151°–152° C. (decomposition).

NMR Spectrum (DMSO-$d_6$) $\delta = 2.0$ (s, 3H, $CH_3$) 4.6 (d, H, J=3Hz; C$\underline{H}$—OH), 5.9 (dd, H, C$\underline{H}$—NH)

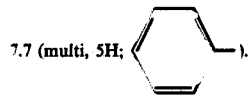

7.7 (multi, 5H;

In addition, broad absorption derived from NH and OH was shown at 6.6–8.0, which was eliminated by the addition of deuterated water.

(2) Preparation of threo-(2RS)-3-acetylamino-2-hydroxy-4-phenyl-butanoic acid

Threo-(2RS)-(3-acetylamino-2-hydroxy-4-oxo-4-phenylbutanoic acid (3.00 g, 0.012 mol) was dissolved in 25 ml of acetic acid. When the solution was hydrogenated with the addition of 0.30 g of 5% palladium carbon and introduction of hydrogen under atmospheric pressure at 60° C., the reaction was completed after about 6 hours.

After separating out the catalyst by filtration, the filtrate was concentrated under reduced pressure. The residue was triturated with 20 ml of ethyl acetate. Deposited crystals were collected by filtration, washed with ethyl acetate and dried in vacuo.

Threo-(2RS)-3-acetylamino-2-hydroxy-4-phenyl-butanoic acid was obtained.
Yield 2.33 g (82.3%).
Mp. 174°–176° C.

In addition, broad absorption derived from OH was shown at 7.0–8.0, which disappeared by the addition of deuterated water.

(3) Preparation of (2S,3R)-3-acetylamino-2-hydroxy-4-phenylbutanoic acid

Threo-(2RS)-3-acetylamino-2-hydroxy-4-phenyl-butanoic acid (10.87 g, 0.046 mol) and 5.55 g (0.046 mol) of S(−)-1-phenylethylamine was dissolved under heating in 90 ml of ethanol and then the solution was allowed to cool at room temperature. Deposited crystals were collected by filtration, washed with a small amount of ethanol and dried in vacuo. 6.37 g of optically impure crystals were obtained.
$[\alpha]_D^{20} + 16.8°$ (c=1, methanol)

The crystals (6.30 g) were dissolved under heating in 100 ml of ethanol and then allowed to cool to room temperature. Deposited crystals were collected by filtration, washed with a small amount of ethanol and dried in vacuo. The S(−)-1-phenylamine salt of (2S,3R)-3-acetylamino-2-hydroxy-phenylbutanoic acid was obtained.

Yield 3.45 g.
Mp. 194°–195° C.
$[\alpha]_D^{20}+29.0°$ (c=1, methanol).

Specific optical rotation of the authetic salt prepared from (2S,3R)-3-acetylamino-2-hydroxy-4-phenylbutanoic acid and S(-)-1-phenylethylamine was as follows:

$[\alpha]_D^{20}+29.1°$ (c=1, methanoll).

(4) Preparation of (2S,3R)-3-amino-2-hydroxy-4-phenylbutanoic acid

The S(-)-1-phenylethylamine salt of (2S,3R)-3-acetylamino-2-hydroxy-4-phenylbutanoic acid (4.25 g, 0.0119 mol) and 1.49 g (0.0178 mol) of sodium hydrogen carbonate were dissolved in 80 ml of water, from which S(-)-1-phenylethylamine was extracted for three times each with 50 ml of ethyl acetate.

The aqueous phase was adjusted with concentrated hydrochloric acid to pH 1–2, and concentrated under reduced pressure to about 40 ml. When the concentrated solution was refluxed under heating with addition of 1.7 ml (0.02 mol) of concentrated hydrochloric acid, the reaction was completed after two hours.

The reaction solution was concentrated to dryness under reduced pressure. The residue was dissolved in 10 ml of water and then concentrated to dryness. The above dissolving and concentrating procedure was repeated.

Finally, the residue was dissolved in 40 ml of water and the solution was adjusted with an aqueous solution of 2 N sodium hydroxide to pH 5–6. After ice cooling, deposited crystals were collected by filtration, washed with cold water and dried in vacuo. (2S,3R)-3-amino-2-hydroxy-4-phenylbutanoic acid was obtained.

Yield 1.48 g (63.8%). $[\alpha]_{578}^{19.5}+32.5°$ (c=0.76, N HCl). The reference value of the compound (J. Med. Chem., 20, 510 (1977)), $[\alpha]_{578}^{20\sim25}+29.5°$ (c=1, N HCl).

(5) Preparation of (2S,3R)-3-benzyloxycarbonylamino-2-hydroxy-4-phenylbutanoic acid (2S,3R)-3-amino-2-hydroxy-4-phenylbutanoic acid (1.45 g, 7.44 mmol), 1.13 g (11.2 mmol) of triethylamine and 2.24 g (8.20 mmol) of benzyl S-4,6-dimethylpyrimidin-2-ylthiolcarbonate were dissolved in a mixed solvent of 7 ml of water and 7 ml of dioxane. When the solution was allowed to react under stirring at room temperature, the reaction was completed after 3 hours.

To the reaction solution was added 20 ml of water and the solution was washed twice each time with 25 ml of ethyl acetate. The aqueous phase was adjusted with diluted hydrochloric acid to pH 1–2. Deposited oily product was extracted twice each time with 30 ml of ethyl acetate. The extracts were joined, washed for three times each time with 30 ml of a common salt aqueous solution and dried over anhydrous sodium sulfate.

After separating out the sodium sulfate by filtration, the filtrate was concentrated to dryness under reduced pressure. The residue was triturated with petroleum ether. Precipitated crystals were collected by filtration, washed with petroleum ether and dried in vacuo. (2S,3R)-3-benzyl-oxycarbonylamino-2-hydroxy-4-phenylbutanoic acid was obtained.

Yield 2.10 g (85.7%).
Mp. 154°–155° C.
$[\alpha]_{578}^{20}+82.5°$ (c=1, acetic acid).

The reference values of the compound (Example 1(1) in Japanese Patent Unexamined Publication No. 136118/1977), Mp. 154.5° C. $[\alpha]_{578}^{24}+83.5°$ (c=1.34, acetic acid).

(6) Preparation of the benzyl ester of (2S,3R)-3-benzyloxy-carbonylamino-2-hydroxy-4-phenylbutanoyl-(S)-leucine (2S,3R)-3-benzyloxycarbonylamino-2-hydroxy-4-phenylbutanoic acid (2.00 g, 6.00 mmol), 2.63 g (6.60 mmol) of the p-toluenesulfonic acid salt of benzyl (S)-leucinate and 0.97 g (7.20 mmol) of 1-hydroxybenzotriazole were dissolved in 20 ml of tetrahydrofuran. While cooling with common salt and ice, 0.67 g (6.6 mmol) of triethylamine and 1.49 g (7.20 mmol) of dicyclohexylcarbodiimide were added and the solution was allowed to react overnight.

Deposited dicyclohexylurea was separated out by filtration and the filtrate was concentrated to dryness under reduced pressure. To the residue was added 50 ml of ethyl acetate. After separating Insoluble products were separated out by filtration and washed with a small amount of ethyl acetate. The filtrate and the washing solution were joined and washed twice with 0.5 N hydrochloric acid, three times with a common salt aqueous solution, twice with 5% sodium hydrogen carbonate aqueous solution and then three times with a common salt aqueous solution successively, and dried over anhydrous sodium sulfate.

After separating the sodium sulfate by filtration, the filtrate was concentrated to dryness under reduced pressure and the residue was triturated with n-hexane. Separated crystals werecollected by filtration, washed with n-hexane and dried in vacuo. The benzyl ester of (2S,3R)-benzyloxycarbonylamino-2-hydroxy-4-phenylbutanoyl-(S)-leucine was obtained.

Yield 3.19 g (99.4%).
Mp. 122°–123° C.
$[\alpha]_{578}^{24}+15.2°$ (c=1, acetic acid).

The reference values of the compound (Example 2(3) in Japanese Patent Unexamined Publication No. 136118/1977)

Mp. 122° C. $[\alpha]_{578}^{23}+15.1°$ (c=0.77, acetic acid).

(7) Preparation of bestatin[(2S,3R)-3-amino-2-hydroxy-4-phenyl-butanoyl-(S)-leucine]

The benzyl ester of (2S,3R)-3-benzyloxycarbonylamino-2-hydroxy-4-phenylbutanoyl-(S)-leucine (3.00 g, 5.60 mmol) was dissolved in 50 ml of 95% acetic acid. When a catalytic amount of palladium black was added to the solution and hydrogen was introduced under atmospheric pressure, the catalytic reduction was completed after two hours. After separating palladium black by filtration, the filtrate was thoroughly concentrated to dryness under reduced pressure and the residue was triturated with 30 ml of acetone. Deposited crystals were separated by filtration and dissolved in 1 N hydrochloric acid. After separating insoluble materials by the addition of a small amount of activated carbon, the filtrate was adjusted with diluted aqueous ammonia to pH 5-6. Precipitated crystals were collected by filtration, washed with acetone and dried in vacuo. Bestatin-[(2S,3R)-3-amino-2-hydroxy-4-phenylbutanoyl-(S)-leucine] was obtained.

Yield 1.47 g (85.0%).

$[\alpha]_{578}^{25} -21.1°$ (c=1, acetic acid).

The reference value of the compound (Example 2(4) in Japanese Patent Unexamined Publication No. 136118/1977), $[\alpha]_{578}^{25} -21.8°$ (c=0.45, acetic acid).

EXAMPLE 20

(1) Preparation of N-hydroxysuccinimide ester of (2S,3R)-3-benzyloxycarbonylamino-2-hydroxy-4-phenylbutanoic acid (2S,3R)-3-benzyloxycarbonylamino-2-hydroxyl-4-phenylbutanoic acid (6.58 g, 0.02 mol) prepared in the same manner as in Example 19(5) and 2.30 g (0.02 mol) of N-hydroxysuccinimide were dissolved in a mixed solvent of 60 ml of dioxane and 60 ml of ethyl acetate. After cooling the solution below 0° C., 4.12 g (0.02 mol) of dicyclohexylcarbodiimide was added and the reaction mixture was allowed to react at the same temperature for 1 hour and then at room temperature overnight.

After separating deposited insoluble compounds by filtration, the filtrate was concentrated under reduced pressure. The residue was solidified with petroleum ether (bp. 30°-70° C. fraction) and re-precipitated from ethyl acetate and petroleum ether. N-hydroxysuccinimide ester of (2S,3R)-3-benzyloxycarbonylamino-2-hydroxy-4-phenylbutanoic acid was obtained.

Yield 6.51 g (76.4%).

Mp. 111°-112° C.

$[\alpha]_{578}^{30} +35.4°$ (c=1.5, acetic acid).

(2) Preparation of (2S,3R)-3-amino-2-hydroxy-4-phenylbutanoyl-(S)-arginine hydrochloride.

The N-hydroxysuccinimide ester of (2S,3R)-3-benzyl-oxycarbonylamino-2-hydroxy-4-phenylbutanoic acid (4.26 g, 0.0] mol) was dissolved in 30 ml of dioxane, to which was added a solution of 2.11 g (0.01 mol) of arginine hydrochloride and 1.40 ml (0.01 mol) of triethylamine in 30 ml of water. The solution was allowed to react at room temperature for 2 days.

After the reaction, the solvent was distilled off under reduced pressure and the residue was dissolved in a solution of chloroform and methanol (1:1 v/v). The solution was subjected to column chromatography using silica gel H type 60 to collect the fractions containing the aimed product and the solvent was distilled off under reduced pressure. Oily (2S,3R)-benzyloxycarbonylamino-2-hydroxy-4-phenylbutanoyl-(S)-arginine hydrochloride was obtained.

Yield 2.02 g (38.7%).

The hydrochloride prepared was dissolved in a mixture of 40 ml of methanol and 20 ml of water. The solution was catalytically reduced at room temperature under atmospheric pressure for 6 hours using palladium black.

After separating out the catalyst by filtration, the filtrate was concentrated under reduced pressure. Acetone was added to the residue to precipitate crystals. The deposited crystals were collected by filtration, washed with acetone and dried in vacuo. (2S,3R)-3-amino-2-nydroxy-4-phenylbutanoyl-(S)-arginine hydrochloride was obtained.

Yield 1.19 g (30.7%)

$[\alpha]_{578}^{30} -6.4°$ (c=1.2, acetic acid).

Rf value 0.08 (Measured on silica gel 60 $F_{254}$ plate (manufactured by Merck) using as a developing solvent n-BuOH:AcOH:H$_2$O=4:1:1).

EXAMPLE 21

Preparation of threo-(2RS)-3-benzoylamino-2-hydroxy-4-oxo-4-phenylbutanoic acid

N-(2-oxo-2-phenylethyl)benzamide (16.7 g, 0.07 mol) and 13.0 g (0.155 mol) of sodium hydrogen carbonate was dissolved in a mixed solvent of 3.75 g (0.13 mol) of 25% glyoxylic acid aqueous solution, 100 ml of water and 250 ml of methanol. The solution was allowed to react at 50°-60° C. overnight.

After separating insoluble products in the reaction solution by filtration, the filtrate was concentrated under reduced pressure to distil off methanol. Diluted hydrochloric acid was added to the concentrated solution to adjust pH 1-2. Deposited crystals were collected by filtration, washed with water and dried in vacuo over phosphorous pentoxide. Crude crystals (17.6 g) were obtained and they were recrystallized with ethyl acetate. Threo-(2RS)-3-benzoylamino-2-hydroxy-4-oxo-4-phenylbutanoic acid was obtained.

Yield 13.5 g (61.8%).

Mp. 174°-176° C. (decomposition).

NMR Spectrum (DMSO-d$_6$): δ=4.6 (d, H, J=4Hz; C$\underline{H}$—OH), 5.9 (dd, H; C$\underline{H}$—NH)

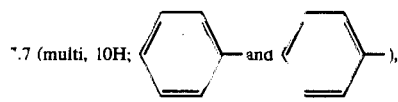

7.7 (multi, 10H;

8.5 (d, H, J=9 Hz; NH).

(2) Preparation of threo-(2RS)-3-benzoylamino-2-hydroxy-4-phenyl butanoic acid

Threo-(2RS)-3-benzoylamino-2-hydroxy-4-oxo-4-phenylbutanoic acid (5.00 g, 0.016 mol) and 0.50 g of 10% palladium carbon were added in 90 ml of acetic acid. When the solution was allowed to react while introducing hydrogen at 70° C. under atmospheric pressure, the reaction was completed after about 8 hours.

After separating out the catalyst by filtration, the filtrate was concentrated under reduced pressure. The oily residue was thoroughly triturated with petroleum ether (bp. 30°-70° C. fraction) and the supernatant liquid was removed by decantation. Upon adding new petroleum ether and rubbing the glass wall with a glass rod under cooling, crystallization occured. After left to stand at room temperature for 1 hour, the crystals were collected by filtration, washed with petroleum ether and dried in vacuo. Threo-(2RS)-3-benzoylamino-2-hydroxy-4-phenylbutanoic acid was obtained.

Yield 4.61 g (96.4%). Mp. 144°-145° C.

NMR Spectrum (DMSO-d$_6$):δ=B 2.9 (d, 2H, J=7 Hz; CH$_2$), 4.0(d,H,J=3 Hz; C$\underline{H}$—OH), 4.55 (multi, H: C$\underline{H}$—NH), 7.25, 7.5 (s, multi, 10H; )

7.95 (d,H,J=8 Hz; NH).

(3) Preparation of (2S,3R)-3-benzoylamino-2-hydroxy-4-phenylbutanoic acid

Threo-(2RS)-3-benzoylamino-2-hydroxy-4-phenylbutanoic acid (6.30 g, 0.0211 mol) and 2.57 g (0.211 mol) of S(−)-1-phenylethylamine were dissolved under heating in 18 ml of ethanol and then left overnight at room temperature.

Deposited crystals were collected by filtration and recrystallized from ethanol. The S(−)-1-phenylethylamine salt of (2S,3R)-3-benzoylamino-2-hydroxy-4-phenylbutanoic acid was obtained.

Yield 1.22 g (27.5%). Mp. 147°–148° C. $[\alpha]_{578}^{29} + 70.6°$ (c=1.02, acetic acid).

Elemental analysis for $C_{25}H_{28}N_2O_4$: Found: C: 71.67, H: 6.99, N: 6.73; Calculated: C: 71.39, H: 6.72, N: 6.67.

The salt prepared (1.00 g, 2.38 mmol) was added to and shaken with a mixture of 20 ml of N sulfuric acid and 50 ml of ethyl acetate. The ethyl acetate phase was separated and washed with water repeatedly till it became neutral. Then the solution was dried over anhydrous magnesium sulfate. After separating out the magnesium sulfate by filtration, the filtrate was concentrated under reduced pressure and the residue was crystallized from ethyl acetate and petroleum ether (bp. 30°–70° C. fraction). Deposited crystals were collected by filtration, washed with the same mixed solvent as above and dried in vacuo. (2S,3R)-3-Benzoylamino-2-hydroxy-4-phenylbutanoic acid was obtained.

Yield 0.64 g.
Mp. 172°–173° C.
$[\alpha]_{578}^{25} + 109.5°$ (c=1.1, acetic acid).

Elemental analysis for $C_{17}H_{17}NO_4$ Found: C: 68.34, H: 5.92, N: 4.44. Calculated: C: 68.19, H: 5.73, N: 4.68.

EXAMPLE 22

(1) Preparation of threo-(2RS)-2-hydroxy-4-oxo-4-phenyl-3-phthaliminobutanoic acid N-(2-oxo-2-phenylethyl)phthalimide (10.0 g, 0.0377 mol) and 9.00 g (0.107 mol) of sodium hydrogen carbonate were dissolved in a mixed solvent of 20.1 g (0.068 mol) of 25% glyoxylic acid aqueous solution and 20 ml of ethanol. The solution was allowed to react at 50°–60° C. for 24 hours.

The reaction solution was concentrated under reduced pressure to distil off ethanol. The concentrated solution was incorporated and shaken with 100 ml of ethyl acetate and 50 ml of 5% sodium hydrogen carbonate aqueous solution. The aqueous phase was separated and adjusted with diluted hydrochloric acid to pH 1–2. Deposited crystals were collected by filtration, washed with water and dried in vacuo over phosphorous pentoxide. Threo-(2RS)-2-hydroxy-4-oxo-4-phenyl-3-phthaliminobanoic acid was obtained.

Yield 1.97 g (15.4%).
Mp. 168°–170° C. (decomposition).
NMR Spectrum (DMSO-d$_6$); δ=4.55 (d, H, J=4 Hz; CH—OH), 5.8 (dd, H; CH—NH), 7.8 (multi, 9H; 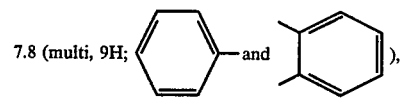),

(2) Preparation of threo-(2RS)-2-hydroxy-4-phenyl-3-phthaliminobutanoic acid Threo-(2RS)-2-hydroxy-4-oxo-4-phenyl-3-phthaliminobutanoic acid (1.00 g, 2.90 mmol) and 0.10 g of 10% palladium black were added to 20 ml of acetic acid. The mixture was catalytically reduced while introducing hydrogen at 70° C. under atmospheric pressure for 5.5 hours.

The reaction mixture was concentrated under reduced pressure. Petroleum ether (bp. 30°–70° C. fraction) and then a small amount of ethyl acetate were added to the residue to crystallize oily product. Deposited crystals were collected by filtration, washed with petroleum ether and dried in vacuo. Threo-(2RS)-2-hydroxy-4-phenyl-3-phthaliminobutanoic acid was obtained.

Yield 0.55 g (57%).
Mp. 97°–103° C. (foaming).
NMR Spectrum (DMSO-d$_6$) δ=2.9 (d, 2H, J=7 Hz; CH$_2$), 3.9 (d, H, J=3 Hz; CH—OH), 4.4 (multi, H; CH—NH), 7.3, 7.5 (s, multi, 9H; 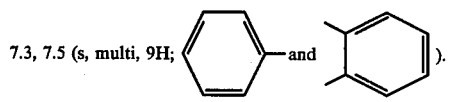).

Other compounds listed in Table 3 were also produced in the procedures analogous to those in Examples 18–22. As the starting material for the compounds of formula (III), corresponding compounds of the formula (I) or (II) were employed. All of the compounds in Table 3 were of threo-(2RS) form.

TABLE 3

| Compounds and physical properties | |
|---|---|
| The compounds of the formula (III) | The compounds of the formula (IV) |
| 23 R$_1$ = phenyl, R$_2$ = chloroacetylamino<br>R$_3$ = hydrogen | R$_1$ = phenyl, R$_2$ = chloroacetylamino<br>R$_3$ = hydrogen |

TABLE 3-continued

Compounds and physical properties

| The compounds of the formula (III) | The compounds of the formula (IV) |
|---|---|
| m.p. 141-142° C. (decomposition)<br>NMR Spectrum (DMSO—d$_6$)<br>δ = 4.2(s,2H; CH$_2$), 4.5(d,H,J=4 Hz; CH—OH),<br>5.7(dd, H; CH—NH), 7.8(multi, 5H; ),<br>8.4(d,H,J=9 Hz; NH). | m.p. 108-110° C.<br>NMR Spectrum (CDCl$_3$)<br>δ = 2.95(d,2H,J=7 Hz; CH$_2$—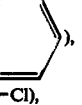),<br>4.0, 4.2(s,d,H,2H; CH—OH, CH$_2$—Cl),<br>4.7(multi, H, CH—NH), 7.15(d,H,J=10 Hz;<br>NH), 7.25(s, 5H, 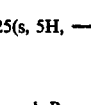). |
| 24 R$_1$ = phenyl, R$_2$ = t-butyloxycarbonylamino<br>R$_3$ = hydrogen  *Note 1<br>m.p. 142-143° C. (decomposition)<br>NMR Spectrum (DMSO—d$_6$)<br>δ = 1.35 (s, 9H; (CH$_3$)$_3$C), 4.3(d,H,J=4 Hz;<br>CH—OH), 5.35(dd, H; CH—NH),<br>6.6(d,H,J=10 Hz; NH), 7.8(multi, 5H; 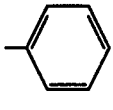) | R$_1$ = phenyl, R$_2$ = t-butyloxycarbonylamino<br>R$_3$ = hydrogen<br>NMR Spectrum (CDCl$_3$)<br>δ = 1.4(s,9H; (CH$_3$)$_3$C), 2.9(d,2H,J=7 Hz;<br>CH$_2$), 4.1(s,H; CH—OH),<br>4.2(multi, H; CH—NH), 7.2(s,5H; 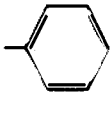). |
| 25 R$_1$ = 3-hydroxyphenyl, R$_2$ = benzoylamino<br>R$_3$ = hydrogen<br>m.p. 176-177° C. (decomposition)<br>NMR Spectrum (DMSO—d$_6$)<br>δ = 4.7(d,H,J=4 Hz; CH—OH), 5.95(dd,H;<br>CH—NH), 7.5(multi, 9H; 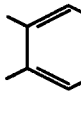, 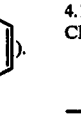).<br>8.4(d,H,J=9 Hz; NH) | R$_1$ = 3-hydroxyphenyl, R$_2$ = benzoylamino<br>R$_3$ = hydrogen<br>m.p. 80-90° C. (foaming), 162-165° C.<br>NMR Spectrum (DMSO—d$_6$)<br>δ = 2.95(d,2H,J=7 Hz; CH$_2$),<br>4.15(d,H,J=2 Hz; CH—OH), 4.7(multi, H;<br>CH—NH), 7.2, 7.4(s, multi, 5H, 4H;<br>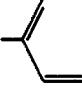, 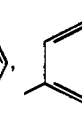). |
| 26 R$_1$ = 4-hydroxyphenyl, R$_2$ = acetylamino<br>R$_3$ = hydrogen<br>m.p. 179-181° C. (decomposition)<br>NMR Spectrum (DMSO—d$_6$)<br>δ = 1.9(s,3H; CH$_3$),<br>4.45 (d,H,J=3 Hz; CH—OH), 5.7(dd, H; CH—NH),<br>6.9, 7.9(dd, 2H,2H,J=8 Hz; 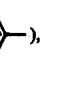),<br>7.95(d,H,J=8 Hz; NH). | R$_1$ = 4-hydroxyphenyl, R$_2$ = acetylamino<br>R$_3$ = hydrogen<br>m.p. 194-197° C. (decomposition)<br>NMR Spectrum (DMSO—d$_6$)<br>δ = 2.3(s,3H; CH$_3$), 3.1(d,2H,J=7 Hz; CH$_2$)<br>4.65(s,H; CH—OH), 4.85(multi, H; CH—NH),<br>6.9, 7.2(d,d,2H,2H,J=8 Hz; 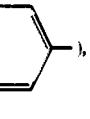),<br>8.6(d,H,J=9 Hz; NH). |
| 27 R$_1$ = phenyl, R$_2$ = chloroacetylamino<br>R$_3$ = methyl<br>m.p. 119-121° C.<br>NMR Spectrum (CDCl$_3$)<br>δ = 3.9(s,3H; CH$_3$), 4.1(s,2H; CH$_2$),<br>4.6(d,H, J=2 Hz; CH—OH), 5.95(dd,H; CH—NH),<br>7.8(multi, 5H; ). | R$_1$ = phenyl, R$_2$ = chloroacetylamino<br>R$_3$ = methyl<br>NMR Spectrum (CDCl$_3$)<br>δ = 2.95(d,2H,J=7 Hz; 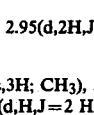—CH$_2$),<br>3.7(s,3H; CH$_3$), 3.95(s,2H; CH$_2$—Cl),<br>4.15(d,H,J=2 Hz; CH—OH),<br>4.6(multi, H; CH—NH), 6.9(d,H,J=9 Hz; NH)<br>7.3(s,5H; 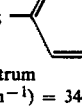).<br>IR Spectrum<br>ν$_{max}^{Film}$(cm$^{-1}$) = 3400 and 3300 (broad),<br>1740 (broad), 1660 (broad), 1605, 1545<br>and 1525 (broad), 1500, 1440, 1410,<br>1270 and 1220 (broad), 1120, 995, 930,<br>915, 860, 750, 700. |

*Note 1
2-t-butoxycarbonylaminoacetophenone used as the starting material was prepared by reacting 2-aminoacetophenone hydrochloride with t-butyl S—4,6-dimethylpyrimidin-2-ylthiolcarbonate and triethylamine in a mixture of dioxane and water (1:1).

EXAMPLE 28

Threo-(2RS)-3-amino-2-hydroxy-4-phenylbutanoic acid (39.00 g, 0.200 mol) prepared from threo-(2RS)-3-acetylamino-2-hydroxy-4-phenylbutanoic acid given by Example 19(2) upon hydrolysis with hydrochloric acid in the same manner as in Example 1(4), 65.80 g (0.240 mol) of benzyl S-4,6-dimethylpyrimidin-2-ylthiolcarbonate and 42.0 ml (0.300 mol) of triethylamine were allowed to react in a mixed solvent of 300 ml of water and 300 ml of dioxane and treated in the same manner as in Example 1(6). Threo-(2RS)-3-benzyloxycarbonylamino-2-hydroxy-4-phenylbutanoic acid was obtained.

Yield 61.30 g (93.2%).
Mp. 133°–134° C.
Elemental analysis for $C_{18}H_{19}NO_5$: Found: C: 65.83, H: 5.77, N: 4.13. Calculation: C: 65.62, H: 5.82, N: 4.26.

Threo-(2RS)-3-benzyloxycarbonylamino-2-hydroxy-4-phenylbutanoic acid (5.73 g, 0.0174 mol) prepared and 7.47 g (0.0174 mol) of brucine monohydrate were dissolved under heating in 100 ml of ethyl acetate and left at room temperature overnight. Deposited crystals were collected by filtration and recrystallized with ethyl acetate. The brucine salt of (2S,3R)-3-benzyloxycarbonylamino-2-hydroxy-4-phenylbutanoic acid was obtained.

Yield 3.58 g (56.9%).
Mp. 144° C.
$[\alpha]_{578}^{31}$ +35.9° (c=1.2, acetic acid).

The brucine salt (2.00 g, 2.63 mmol) obtained was dissolved in and shaken with a mixture of 50 ml of N hydrochloric acid and 100 ml of ethyl acetate. The ethyl acetate phase was separated and washed with water repeatedly till it became neutral. Then the solution was dried over anhydrous magnesium sulfate. After separating out the magnesium sulfate by filtration, the filtrate was concentrated under reduced pressure. The residue was crystallized from ethyl acetate and petroleum ether (bp. 30°–70° C. fraction). Deposited crystals were collected by filtration, washed with the same mixed solvent as above and dried in vacuo. (2S,3R)-3-benzyloxycarbonylamino-2-hydroxy-4-phenylbutanoic acid was obtained.

Yield 0.77 g.
Mp. 154°–155° C.
$[\alpha]_{578}^{25}$ +83.0° (c=1.0, acetic acid).
Rf value (Example 1(2) in Japanese Patent Unexamined Publication No. 136118/1977)
Mp. 154.5° C. $[\alpha]_{578}^{24}$ +83.5° (c=1.34, acetic acid).

What is claimed is:
1. (2S,3R)-3-amino-2-hydroxy-4-(4-methoxyphenyl)-butanoyl-(S)-leucine.

* * * * *